(12) United States Patent
Pancholy et al.

(10) Patent No.: US 11,653,931 B2
(45) Date of Patent: *May 23, 2023

(54) APPARATUS AND METHOD TO STOP BLEEDING

(71) Applicants: Samir Bipin Pancholy, Clarks Summit, PA (US); Nolan Rajendra Sardesai, Arcadia, CA (US); Milind Padmakar Panse, Riverside, CA (US); Rajendra Gurudas Sardesai, Arcadia, CA (US)

(72) Inventors: Samir Bipin Pancholy, Clarks Summit, PA (US); Nolan Rajendra Sardesai, Arcadia, CA (US); Milind Padmakar Panse, Riverside, CA (US); Rajendra Gurudas Sardesai, Arcadia, CA (US)

(73) Assignee: Vasoinnovations, Inc., South Pasadena, CA (US)

( * ) Notice: Subject to any disclaimer, the term of this patent is extended or adjusted under 35 U.S.C. 154(b) by 245 days.

This patent is subject to a terminal disclaimer.

(21) Appl. No.: 17/117,061

(22) Filed: Dec. 9, 2020

(65) Prior Publication Data
US 2021/0085337 A1  Mar. 25, 2021

Related U.S. Application Data

(63) Continuation of application No. 16/179,044, filed on Nov. 2, 2018, now Pat. No. 10,888,334, which is a
(Continued)

(51) Int. Cl.
*A61B 17/135* (2006.01)
*A61B 17/132* (2006.01)
(Continued)

(52) U.S. Cl.
CPC ........ *A61B 17/1325* (2013.01); *A61B 5/0261* (2013.01); *A61B 5/0295* (2013.01); *A61B 17/135* (2013.01); *A61B 2017/12004* (2013.01)

(58) Field of Classification Search
CPC .............. A61B 17/132; A61B 17/1322; A61B 17/1325; A61B 17/135; A61B 2017/12004; A61B 5/0261; A61B 5/0295
See application file for complete search history.

(56) References Cited

U.S. PATENT DOCUMENTS

| | | | |
|---|---|---|---|
| 37,156 | A | 12/1862 | Dunton |
| 3,905,361 | A | 9/1975 | Hewson et al. |

(Continued)

FOREIGN PATENT DOCUMENTS

| | | |
|---|---|---|
| EP | 0 601 756 A1 | 6/1994 |
| EP | 1 382 306 A2 | 1/2004 |

(Continued)

OTHER PUBLICATIONS

International Search Report in International application No. PCT/US 16/45207.
(Continued)

*Primary Examiner* — Ryan J. Severson
(74) *Attorney, Agent, or Firm* — Rajendra Gurudas Sardesai

(57) ABSTRACT

A hemostatic device is provided to stop bleeding at a puncture site on an artery of a patient, the device comprising a transparent flexible band to be wrapped at the site where the bleeding is to be stopped, a curved compression member having an inner peripheral side and possessing a first curved portion in its first half and a second curved portion in its second half, a first balloon provided on the inner peripheral side in the first half of the curved compression member and a second balloon provided on the inner peripheral side in the second half of the curved compression member. The bleeding from a first artery is stopped by compressing the first artery at the puncture site using inflation of the first balloon
(Continued)

and blood flow in the first artery is increased by compression of a second artery using inflation of the second balloon.

20 Claims, 30 Drawing Sheets

Related U.S. Application Data continuation of application No. 15/487,661, filed on Apr. 14, 2017, now Pat. No. 10,213,213, which is a continuation of application No. 15/099,603, filed on Apr. 15, 2016, now Pat. No. 9,642,628, which is a continuation of application No. 14/819,383, filed on Aug. 5, 2015, now Pat. No. 9,332,994, which is a continuation-in-part of application No. 13/941,219, filed on Jul. 12, 2013, now Pat. No. 9,308,000.

(60) Provisional application No. 62/157,419, filed on May 5, 2015, provisional application No. 62/142,195, filed on Apr. 2, 2015, provisional application No. 62/103,063, filed on Jan. 13, 2015, provisional application No. 62/096,857, filed on Dec. 25, 2014, provisional application No. 62/089,281, filed on Dec. 9, 2014.

(51) Int. Cl.
  *A61B 5/026* (2006.01)
  *A61B 5/0295* (2006.01)
  *A61B 17/12* (2006.01)

(56) References Cited

U.S. PATENT DOCUMENTS

| | | | |
|---|---|---|---|
| 4,469,099 A | 9/1984 | McEwen | |
| 4,863,429 A | 9/1989 | Baldwin | |
| 4,920,971 A | 5/1990 | Blessinger | |
| 4,981,133 A | 1/1991 | Rollband | |
| 5,152,302 A | 10/1992 | Fareed | |
| 5,295,951 A | 3/1994 | Fareed | |
| 5,307,811 A | 5/1994 | Sigwart et al. | |
| 5,413,582 A | 5/1995 | Eaton | |
| 5,433,724 A | 7/1995 | Kawasaki et al. | |
| 5,464,420 A | 11/1995 | Hori et al. | |
| 5,486,194 A | 1/1996 | Kawasaki et al. | |
| 5,496,262 A | 3/1996 | Johnson et al. | |
| 5,514,155 A | 5/1996 | Daneshvar | |
| 5,569,297 A | 10/1996 | Makower et al. | |
| 5,643,315 A | 7/1997 | Daneshvar | |
| 5,660,182 A | 8/1997 | Kuroshaki et al. | |
| 5,690,610 A | 11/1997 | Ito et al. | |
| 5,779,657 A | 7/1998 | Daneshvar | |
| 5,792,173 A | 8/1998 | Breen et al. | |
| 5,840,037 A | 11/1998 | Tochikubo et al. | |
| 6,007,562 A | 12/1999 | Harren et al. | |
| 6,336,901 B1 | 1/2002 | Itonaga et al. | |
| 6,361,496 B1 | 3/2002 | Zikorus et al. | |
| 6,527,727 B2 | 3/2003 | Itonaga et al. | |
| 6,694,821 B2 | 2/2004 | Yamakoshi et al. | |
| 6,827,727 B2 | 12/2004 | Stalemark et al. | |
| 7,498,477 B2 | 3/2009 | Wada et al. | |
| 7,927,295 B2 | 4/2011 | Bates et al. | |
| 8,034,009 B2 | 10/2011 | Bates et al. | |
| 8,152,776 B2 | 4/2012 | McCluskey | |
| 8,481,803 B2 | 7/2013 | Wada et al. | |
| 8,481,805 B2 | 7/2013 | Wada et al. | |
| 8,524,974 B2 | 9/2013 | Wada et al. | |
| 8,759,603 B2 | 6/2014 | Wada et al. | |
| 9,308,000 B2* | 4/2016 | Pancholy | A61B 17/12 |
| 9,332,994 B2* | 5/2016 | Pancholy | A61B 17/1325 |
| 9,408,611 B1* | 8/2016 | Pancholy | A61B 17/1325 |
| 9,510,838 B2* | 12/2016 | Pancholy | A61B 17/135 |
| 9,592,060 B2* | 3/2017 | Pancholy | A61B 17/1325 |
| 9,642,628 B2* | 5/2017 | Pancholy | A61B 90/92 |
| 9,668,744 B2* | 6/2017 | Pancholy | A61B 17/3215 |
| 9,895,155 B2 | 2/2018 | Wada et al. | |
| 9,949,738 B2* | 4/2018 | Pancholy | A61B 17/12 |
| 10,117,672 B2* | 11/2018 | Pancholy | A61B 17/1325 |
| 10,213,212 B2* | 2/2019 | Pancholy | A61B 17/12 |
| 10,213,213 B2* | 2/2019 | Pancholy | A61B 90/92 |
| 10,213,214 B2* | 2/2019 | Pancholy | A61B 17/135 |
| 10,245,041 B2* | 4/2019 | Pancholy | A61B 17/12009 |
| 10,335,161 B2* | 7/2019 | Pancholy | A61B 5/0295 |
| 10,342,545 B2* | 7/2019 | Pancholy | A61B 17/12009 |
| 10,342,551 B2* | 7/2019 | Pancholy | A61B 17/12 |
| 10,349,951 B2* | 7/2019 | Pancholy | A61B 17/135 |
| 10,357,254 B2* | 7/2019 | Pancholy | A61B 17/1325 |
| 10,507,026 B2* | 12/2019 | Pancholy | A61B 5/0295 |
| 10,639,042 B2* | 5/2020 | Pancholy | A61B 17/1325 |
| 10,716,576 B2* | 7/2020 | Pancholy | A61B 17/135 |
| 10,722,245 B2* | 7/2020 | Pancholy | A61B 17/12 |
| 10,722,246 B2* | 7/2020 | Pancholy | A61B 17/12009 |
| 10,779,840 B2* | 9/2020 | Hazama | A61B 17/1325 |
| 10,888,334 B2* | 1/2021 | Pancholy | A61B 5/0261 |
| 2002/0115603 A1 | 8/2002 | Whitehouse | |
| 2002/0147404 A1 | 10/2002 | Kato | |
| 2002/0170359 A1 | 11/2002 | Yamakoshi et al. | |
| 2003/0199922 A1 | 10/2003 | Buckman | |
| 2004/0049214 A1 | 3/2004 | Akerfeldt | |
| 2004/0098035 A1 | 5/2004 | Wada | |
| 2004/0122469 A1 | 6/2004 | Akerfeldt | |
| 2004/0193059 A1 | 9/2004 | Inoue et al. | |
| 2005/0153090 A1 | 7/2005 | Marchitto | |
| 2006/0149153 A1 | 7/2006 | Shirasaki et al. | |
| 2009/0138039 A1 | 5/2009 | Wada et al. | |
| 2009/0234261 A1 | 9/2009 | Singh | |
| 2009/0281565 A1 | 11/2009 | McNeese | |
| 2010/0179586 A1 | 7/2010 | Ward et al. | |
| 2012/0071804 A1 | 3/2012 | Philip et al. | |
| 2012/0296369 A1 | 11/2012 | Atthoff et al. | |
| 2013/0116725 A1 | 5/2013 | Wada et al. | |
| 2013/0178894 A1 | 7/2013 | Wada et al. | |
| 2013/0237866 A1 | 9/2013 | Cohen | |
| 2013/0245674 A1 | 9/2013 | Wada et al. | |
| 2013/0245675 A1 | 9/2013 | Wada et al. | |
| 2013/0282048 A1 | 10/2013 | Wada et al. | |
| 2013/0289613 A1 | 10/2013 | Wada et al. | |
| 2014/0142615 A1 | 5/2014 | Corrigan, Jr. | |
| 2015/0018869 A1 | 1/2015 | Benz | |
| 2015/0201948 A1 | 7/2015 | Kornowski et al. | |
| 2016/0174952 A1 | 7/2016 | Shah | |
| 2016/0213373 A1 | 7/2016 | Drasler et al. | |
| 2016/0338709 A1 | 11/2016 | Wada et al. | |
| 2018/0000491 A1 | 1/2018 | Wada et al. | |
| 2018/0000492 A1 | 1/2018 | Wada et al. | |
| 2018/0000493 A1 | 1/2018 | Wada et al. | |
| 2018/0000494 A1 | 1/2018 | Wada et al. | |
| 2018/0014833 A1 | 1/2018 | Wada et al. | |
| 2019/0069905 A1* | 3/2019 | Pancholy | A61B 5/0295 |
| 2021/0085337 A1* | 3/2021 | Pancholy | A61B 5/0261 |

FOREIGN PATENT DOCUMENTS

| | | |
|---|---|---|
| EP | 2 070 483 A2 | 6/2009 |
| EP | 2 245 998 A1 | 11/2010 |
| GB | 2486194 A | 6/2012 |
| JP | 56-33526 Y2 | 8/1981 |
| JP | 5-305093 A | 11/1993 |
| JP | 7-79983 A | 3/1995 |
| JP | 8-71077 A | 3/1996 |
| JP | 8-140990 A | 6/1996 |
| JP | 3031486 U | 9/1996 |
| JP | 10-57386 A | 3/1998 |
| JP | 2000-515773 A | 11/2000 |
| SG | 178650 A1 | 3/2012 |
| WO | WO 97/02783 A1 | 1/1997 |
| WO | WO-97/17900 A1 | 5/1997 |
| WO | WO-2012/126154 A1 | 9/2012 |

(56) References Cited

OTHER PUBLICATIONS

Written Opinion of the International Searching Authority in International application No. PCT/US 16/45207.
European Search Report Application No. EP 16181506.
International Preliminary Report on Patentability (Chapter 1 of PCT) International Application No. PCT/US2016/041801.
International Preliminary Report on Patentability (Chapter 1 of PCT) International Application No. PCT/US2016/045207.
Extended European Search Report Application No. EP 16833489.
Pancholy, S et al "A technique to access difficult to find upper extremity veins for right heart catheterization . . . " Catheter Cardiovasc Interv., 78(5):809-12, Nov. 2011.
Patel, T et al, "Reaccessing an occluded radial artery: a "proximal entry" technique" J Interv Cardiol. 24(4):378-81, Aug. 2011.
Patel, T et al, "Management of radial and brachial artery perforations during transradial procedures . . . " J Invasive Cardiol. 21(10):544-7, Oct. 2009.
Patel, T et al, "A simple approach for the reduction of knotted coronary catheter in radial artery during transradial approach" J Invasive Cardiol. 23(5):E126-7, May 2011.
Examiner's Search in priority U.S. Appl. No. 13/941,219, filed Jul. 12, 2013—Other References Patent.
Examiner's Search in priority U.S. Appl. No. 13/941,219, filed Jul. 12, 2013—Other References NPL.
Examiner's Search in priority U.S. Appl. No. 13/941,219, filed Jul. 12, 2013—Other References Inventor.
Extended European Search Report Application No. EP 18163282.
Letter regarding Commonly Assigned Copending and Allowed Applications.
U.S. Appl. No. 13/941,219, filed Jul. 12, 2013, now U.S. Pat. No. 9,308,000.
U.S. Appl. No. 14/819,383, filed Aug. 5, 2015, now U.S. Pat. No. 9,332,994.
U.S. Appl. No. 15/062,150, filed Mar. 6, 2016, now U.S. Pat. No. 9,510,838.
U.S. Appl. No. 15/093,739, filed Apr. 8, 2016, now U.S. Pat. No. 9,408,611.
U.S. Appl. No. 15/099,603, filed Apr. 15, 2016, now U.S. Pat. No. 9,642,628.
U.S. Appl. No. 15/150,394, filed May 9, 2016, now U.S. Pat. No. 9,668,744.
U.S. Appl. No. 15/340,023, filed Nov. 1, 2016, now U.S. Pat. No. 9,592,060.
U.S. Appl. No. 15/417,480, filed Jan. 27, 2017, now U.S. Pat. No. 10,213,212.
U.S. Appl. No. 15/426,056, filed Feb. 7, 2017, now U.S. Pat. No. 9,949,738.
U.S. Appl. No. 15/487,661, filed Apr. 14, 2017, now U.S. Pat. No. 10,213,213.
U.S. Appl. No. 15/588,586, filed May 5, 2017, now U.S. Pat. No. 10,335,161.
U.S. Appl. No. 15/630,920, filed Jun. 22, 2017, now U.S. Pat. No. 10,349,951.
U.S. Appl. No. 15/708,123, filed Sep. 18, 2017, now U.S. Pat. No. 10,342,551.
U.S. Appl. No. 15/898,591, filed Feb. 18, 2018, now U.S. Pat. No. 10,117,672.
U.S. Appl. No. 15/924,273, filed Mar. 18, 2018, now U.S. Pat. No. 10,639,042.
U.S. Appl. No. 16/056,261, filed Aug. 6, 2018, now U.S. Pat. No. 10,357,254.
U.S. Appl. No. 16/130,201, filed Sep. 13, 2018, now abandoned.
U.S. Appl. No. 16/130,959, filed Sep. 13, 2018, now U.S. Pat. No. 10,507,026.
U.S. Appl. No. 16/134,091, filed Sep. 18, 2018, now U.S. Pat. No. 10,342,545.
U.S. Appl. No. 16/136,913, filed Sep. 20, 2018, now U.S. Pat. No. 10,245,041.
U.S. Appl. No. 16/138,958, filed Sep. 21, 2018, now U.S. Pat. No. 10,213,214.
U.S. Appl. No. 16/179,044, filed Nov. 2, 2018, now U.S. Pat. No. 10,888,334.
U.S. Appl. No. 16/252,725, filed Jan. 21, 2019, now U.S. Pat. No. 10,987,109.
U.S. Appl. No. 16/254,589, filed Jan. 23, 2019, now U.S. Pat. No. 10,722,245.
U.S. Appl. No. 16/255,834, filed Jan. 23, 2019, now U.S. Pat. No. 10,716,576.
U.S. Appl. No. 16/281,129, filed Feb. 21, 2019, now U.S. Pat. No. 10,722,246.
U.S. Appl. No. 16/829,317, filed Mar. 25, 2020.
U.S. Appl. No. 16/888,792, filed May 31, 2020.
U.S. Appl. No. 16/910,048, filed Jun. 23, 2020.
U.S. Appl. No. 17/005,262, filed Aug. 27, 2020.
U.S. Appl. No. 17/124,133, filed Dec. 16, 2020.
U.S. Appl. No. 17/222,988, filed Apr. 5, 2021.
Pancholy, S., "Radial Artery Hemostasis and Occlusion", Presentation, TCT 2012, Miami, FL.
Pancholy, S., "Radial Shealth Removal and Prevention of Radial Occlusion", Presentation, TCT 2012, Miami, FL.
Samir Pancholy, et al, "Prevention of Radial Artery Occlusion—Patent Hemostasis Evaluation Trial (PROPHET study)" Catheterization and Cardiovascular Interv 72:335-340 (2008).
Samir B. Pancholy, "Transradial Access in an Occluded Radial Artery: New Technique" Journal Invasive Cardiology, vol. 19, Issue 12, Dec. 2007.
Samir B. Pancholy, "Transradial Approach" Angioplasty.Org Interview Series, 3 pages, Aug. 2008.
Samir B. Pancholy, "Impact of Two Different Hemostatic Devices on Radial Artery Outcomes after Transradial Catheterization" J Invasive Cardiology,vol. 21,Issue 3, Mar. 2009.
Ivo Bernat, et al, "Efficacy and Safety of Transient Ulnar Artery Compression to Recanalize Actute Radial Artery Occlusion . . . " Am J Cardiol,107:1698-1701(2011).
Samir B. Pancholy, "Strategies to Prevent Radial Artery Occlusion After Transradial PCI" Curr Cardiol Rep, 16:505, Jun. 2014.
Patel, T. et al, "Balloon-assisted tracking: A must-know technique . . . " Cath. Cardio. Interv., Wileyonlinelibrary.com; DOI:10.1002/ccd.24959, Apr. 2013.
Kwan, T. et al, "Transulnar catheterization in patients with ipsilateral radial artery occlusion" Cath Cardio Interv, Wileyonlinelibrary.com, DOI 10.1002/ccd.24662 Sep. 2012.
Patel, T. et al, "Balloon-assisted tracking of a guide catheter . . . : A technical report" Cath. Cardio. Interv., Wileyonlinelibrary.com; DOI 10.1002/ccd.24504, May 2012.
Kwan, T. et al. "Feasibility and safety of 7F sheathless guiding catheter during transradial coronary intervention", Wileyonlinelibrary.com; DOI 10.1002/ccd.24310, Aug. 2012.
Pancholy, S et al, "Comparison of a priori versus provisional heparin therapy on radial artery occlusion . . . (PHARAOH Study)", Am J Cardiol, vol. 110(2), p. 173-176 Jul. 2012.
Pancholy, S et al, "Radial artery access technique evaluation trial: randomized comparison . . . ", Catheter Cardiovasc Interv., vol. 80(2), p. 288-91, Aug. 2012.
Pancholy, S et al, "Effect of duration of hemostatic compression on radial artery occlusion after transradial access", Catheter Cardio Interv, vol. 79(1), p. 78-81, Jan. 2012.
Caputo, R, et al, "Transradial arterial access for coronary and peripheral procedures . . . " Catheter Cardiovasc Interv., vol. 78(6), p. 823-39, Nov. 2011.
Bertrand, O et al, "Transradial approach for coronary angiography and interventions . . . ", JACC Cardiovasc Interv., vol. 3(10), p. 1022-31 Oct. 2010.
Pancholy, S et al, "Comparison of door-to-balloon times for primary PCI using transradial versus transfemoral approach" Catheter Cardio Interv. vol. 75(7), p. 991-5 Jun. 2010.
International Search Report in International application No. PCT/US 16/41801.
Written Opinion of the International Searching Authority in International application No. PCT/US 16/41801.
Search History in International application No. PCT/US 1641801.

(56) References Cited

OTHER PUBLICATIONS

U.S. Appl. No. 13/933,025, filed Jul. 1, 2013, Wada et al.
U.S. Appl. No. 13/889,101, filed May 7, 2013, Wada et al.
U.S. Appl. No. 13/889,112, filed May 7, 2013, Wada et al.
U.S. Appl. No. 15/229,455, filed Aug. 5, 2016, Wada et al.
U.S. Appl. No. 15/705,483, filed Sep. 15, 2017, Wada et al.
U.S. Appl. No. 15/705,570, filed Sep. 15, 2017, Wada et al.
U.S. Appl. No. 15/705,994, filed Sep. 15, 2017, Wada et al.
U.S. Appl. No. 15/706,301, filed Sep. 15, 2017, Wada et al.
U.S. Appl. No. 15/706,397, filed Sep. 15, 2017, Wada et al.
Patel, T et al, "Contralateral transradial approach for carotid artery stenting: a feasibility study" J. Catheter Cardiovasc Interv. vol. 75(2), p. 268-75. Feb. 2010.
Pancholy, S. "Comparison of the effect of intra-arterial versus intravenous heparin on radial artery occlusion . . . " Am J Cardiol. vol. 104(8) p. 1083-5 Oct. 2009.
Pancholy, S. "Prevention of Radial Artery Occlusion:Prophylactic Hyperperfusion Evaluation Trial ( PROPHET-II )" ClinicalTrial. Gov, Protocol Registration System, Mar. 2012.
Pancholy, S. et al, "Subcutaneous administration of nitroglycerin to facilitate radial artery cannulation" Catheter Cardiovasc Interv. vol. 68(3) p. 389-9, Sep. 2006.
Mamas, M, "Dissection, Occlusion, and Spasm; Myths Involving Sheathless Guide Catheters" Catheterization and Cardiovascular Interventions 76:777-778, Feb. 2010.
Pancholy, S "Hemostasis and Radial Artery Patency", Presentation, http://www.slideshare.net/theradialist/pancholy-sb-201111, Jan. 2012.
Shroff, A et al "Comparing radial with femoral artery access in patients with ST-segment elevation myocardial infarction . . . " Expert Rev Cardio Ther. 11(5):525-7, May 2013.
Patel, T et al "Coronary cannulation through mirror-image right aortic arch during right transradial approach . . . " J Invasive Cardiol. 24(5):234-5, May 2012.
Kwan, T. et al "Balloon-assisted sheathless transradial intervention (BASTI) using 5 Fr guiding catheters" J Invasive Cardiol. 24(5):231-3, May 2012.
Dharma, S. et al "Nitroglycerin plus diltiazem versus nitroglycerin alone for spasm prophylaxis with transradial approach" J Invasive Cardiol. 24(3):122-5, Mar. 2012.
Pancholy, S. et al Prevention of radial artery occulusion . . . , The PROPHET-II Randomized trial, JACC: Cardiovascular Interventions, vol. 9 (19), pp. 1992-1999, Oct. 2016.
Maden, O. et al "Relation between end-procedural activated clotting time values . . . after transradial catheterization" Am. J. Cardiol., vol. 118, pp. 1455-1459 (2016).
Hahalis, G. et al "A comparison of low versus standard heparin dose . . . after 5 French coronary angiography" Int. J. Cardiol. vol. 187, pp. 404-410 (2015).
Aykan, A. et al "Comparison of low dose versus standard dose heparin for radial approach in elective coronary angiography" Int. J. Cardiol. vol. 187, pp. 389-392 (2015).
Uhlemann, M. et al. "The leipzig prospective vascular ultrasound registry in radial artery catheterization", JACC: Cardiovascular Interventions, vol. 5, No. 1, pp. 36-43 (2012).
Roghani, R. et al. "The effect of low dose versus standard dose of arterial heparin . . . randomized clinical trial", ARYA Atheroscler, vol. 12 (1), pp. 10-17 (2016).
Kiemeneij, F. et al. "The PROPHET-II's Prophecy", JACC: Cardiovascular Interventions, vol. 9, No. 19, pp. 2000-2001, Oct. 2016.

* cited by examiner

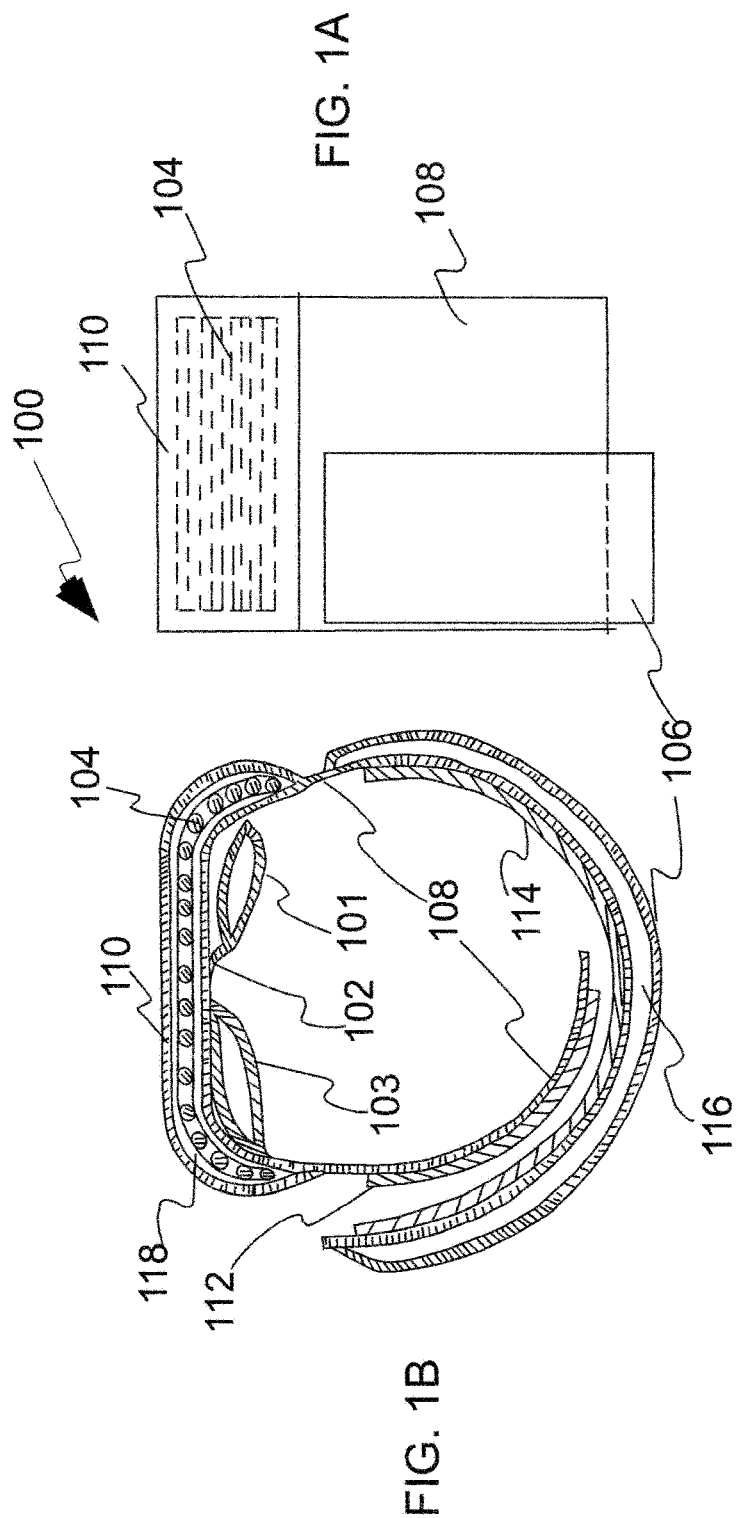

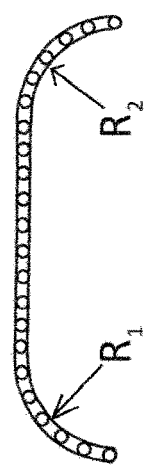
FIG. 2C
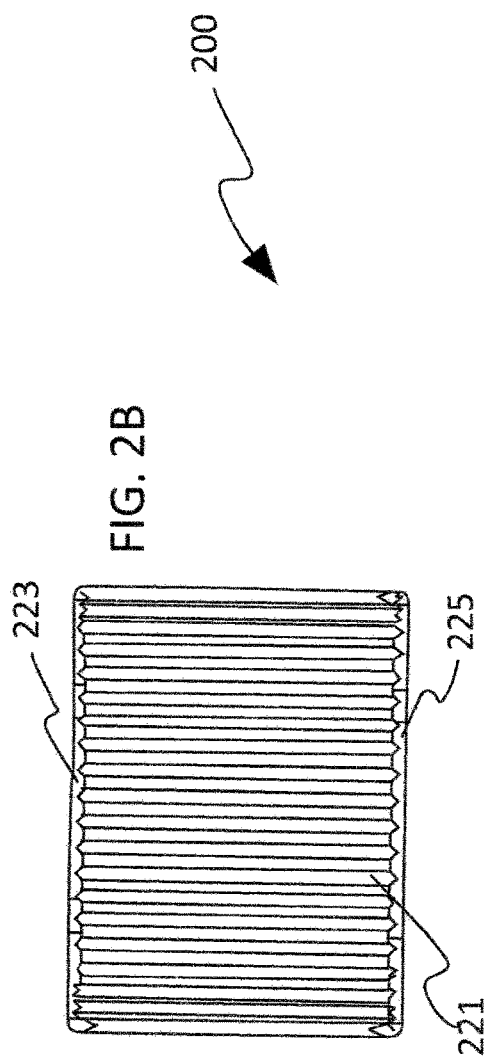
FIG. 2B
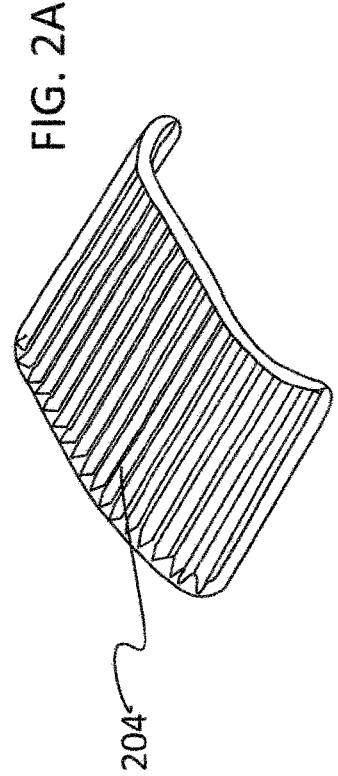
FIG. 2A
FIG. 2

APPARATUS AND METHOD TO STOP BLEEDING

CROSS-REFERENCE TO RELATED APPLICATIONS

This application is a continuation of application U.S. patent application Ser. No. 16/179,044 filed Nov. 2, 2018, which is a continuation of U.S. patent application Ser. No. 15/487,661 filed Apr. 14, 2017, now U.S. Pat. No. 10,213,213, which is a continuation of
U.S. patent application Ser. No. 15/099,603 filed Apr. 15, 2016, now U.S. Pat. No. 9,642,628, which is a continuation of
U.S. patent application Ser. No. 14/819,383, filed Aug. 5, 2015, now U.S. Pat. No. 9,332,994, which is a continuation-in-part of
U.S. patent application Ser. No. 13/941,219, filed Jul. 12, 2013, now U.S. Pat. No. 9,308,000, and claims priority from and benefit of
U.S. Provisional Patent Application No. 62/089,281, filed Dec. 9, 2014,
U.S. Provisional Patent Application No. 62/096,857, filed Dec. 25, 2014,
U.S. Provisional Patent Application No. 62/103,063, filed Jan. 13, 2015,
U.S. Provisional Patent Application No. 62/142,195, filed Apr. 2, 2015, and
U.S. Provisional Patent Application No. 62/157,419, filed May 5, 2015,
the entire contents of all the above listed applications are incorporated herein by reference. The above listed US Provisional Patent Applications were incorporated by reference in priority U.S. patent application Ser. No. 14/819,383, filed Aug. 5, 2015.

FIELD

Embodiments described herein concern devices and methods for obtaining hemostasis after puncturing a blood pathway, including without limitation puncture of radial or ulnar artery.

BACKGROUND

Blood vessel puncture is commonly needed for performance of endovascular procedures. Smaller caliber arteries, including radial, ulnar and pedal arteries, are easier to manage after the procedure because bleeding can be controlled more easily with external pressure. However, occlusion of these arteries occurs more frequently compared to larger arteries, which frequently results in permanent loss of patency.

Radial artery occlusion refers to the blockage of the radial artery and is a consequence of radial artery cannulation that obliterates the radial artery lumen. Hemostatic devices, which are attached by being wrapped around the portion of an arm where the puncture site (also referred to as the access site) is located and compress the puncture site where bleeding is to be stopped, are already known in the prior art (e.g., U.S. Pat. No. 7,498,477 B2, U.S. Pat. Nos. 8,481,803, 8,481,805, JP 3,031,486 U). In prior-art hemostatic devices, pressure applied to the puncture site may lead to radial artery occlusion making it not available for access in the future.

Radial artery occlusion, after transradial access occurs in 2-10% of patients, and is frequently associated with obliteration of radial artery lumen, making that radial artery not suitable for future access for endovascular procedures, invasive monitoring, or its utility as a bypass conduit. Prevention of radial artery occlusion is of paramount importance to avoid loss of a major source of blood supply, future repeat access and other utilities of radial artery, after transradial access. Maintenance of radial artery flow during hemostatic compression has been shown to lower the risk of radial artery occlusion (PROPHET Trial, Pancholy S et al, Catheterization and Cardiovascular Interventions 2008:72(3); 335-340). A decrease in duration of compression has also been shown to lower the risk of radial artery occlusion (Pancholy S et al, Catheterization and Cardiovascular Interventions 2012:79(1):78-81). Thus maintaining blood flow in the radial artery, while compressing the access site after instrumentation, is known to reduce the risk of post-instrumentation radial artery occlusion. Patent hemostasis is therefore understood to mean achieving the cessation of bleeding at the cannulation wound (access site) of the radial artery, while blood is allowed to flow through that artery.

In an article entitled Efficacy and Safety of Transient Ulnar Artery Compression to Recanalize Acute Radial Artery Occlusion After Transradial Catheterization (Am J Cardiol 2011; 107:1698-1701) Ivo Bernat, MD and others discuss a method directed to open an occluded radial artery after the radial artery becomes occluded. In this study, in patients with radial artery occlusion, 3-4 hours after hemostasis of the radial artery, ulnar artery compression was applied to attempt recanalization of radial artery. Bernat et. al. achieved higher success rates at reopening of the radial artery by administration of heparin and compression of the ipsilateral ulnar artery.

SUMMARY

Transradial, as well as transulnar, puncture is increasingly used for obtaining vascular access for endovascular procedures. In one embodiment, a hemostatic device comprises two balloons wherein, after transradial access, the bleeding from the radial artery is stopped by compressing the radial artery at the puncture site using inflation of a first balloon and the radial artery flow is increased by occlusive compression of ipsilateral ulnar artery using inflation of a second balloon. The method maintains blood flow in the radial artery while compressing the access site, after removal of catheter, thereby reducing the risk of post-instrumentation radial artery occlusion. In one embodiment, the first balloon is located over the radial artery to cover a puncture site that is generally about 2 cm. from the base of a palm, and the second balloon is located over the ulnar artery at a position proximate to the base of the palm (Guyon's canal) thereby compressing the ulnar artery at a location where it is most accessible for compression.

In another embodiment, two balloons are part of a band and the band is wrapped around a limb. The center of the first balloon and the center of the second balloon are offset from each other in relation to the central line of axis of the band. In yet another embodiment, the first balloon is larger than the second balloon. In another embodiment, the balloons are rectangular in shape. In one embodiment, the first balloon extends the entire width of the band. In one embodiment, the width of the band is greater than 40 mm. In another embodiment, the width of the band is greater than 45 mm. In yet another embodiment, the band has a width of about 55 mm.

In another embodiment, the hemostatic device comprises a flexible band adapted to be wrapped and secured around a hand of a patient at a site on the hand where bleeding is to be stopped, a compression member having an inner peripheral side, which compression member is made of a material more rigid than the band, a first balloon provided on the inner peripheral side at a position deviated to the center portion of the compression member in lengthwise direction of the band, and the first balloon is connected to the band by a connector on a side of the first balloon adjacent the center portion of the compression member, wherein the first balloon inflates when a fluid is introduced therein; and a second balloon provided on the inner peripheral side of the compression member at a position deviated to an edge of the compression member from the center portion of the compression member in widthwise direction of the band, and the second balloon is connected to the band by a connector on a side of the second balloon adjacent to the edge of the compression member, wherein the second balloon inflates when a fluid is introduced therein. In one embodiment, the compression member is a curved frame with rungs. In some embodiments, rungs may be equidistant from each other along the length of the frame. In other embodiments, the rungs may be staggered whereby some rungs are close to each other while the others are spread out. In yet another embodiment, the compression member is a curved plate.

In some embodiments, at least a portion of the compression member is curved toward the inner peripheral side at proximal and distal ends of the compression member. In one embodiment, the radius of curvature of the compression member at proximal end is nearly the same as radius of curvature of the compression member at distal end. In another embodiment, the compression member may have a contoured shape whereby the band presses snugly the wrist and the base of the palm, and the contoured shape facilitates compression of the ulnar artery at the base of the palm.

In yet another embodiment, multiple rods are placed in pockets that are formed along the length of the band. In another embodiment, multiple planks or flat plates are placed in the pockets. In one embodiment, the rods or planks are made of material that is more rigid than the band and maintains a substantially fixed shape. The length of the rods is about the same as the width of the band, and when the rods are placed in the pockets, they cover the width of the band. In another embodiment, a sleeve is formed covering the pockets holding the rods and a frame is placed in the sleeve. In yet another embodiment, the material of the frame is less rigid than the material of the rods and more rigid than the material of the band. In another embodiment, the compression member has at least one flat plate connected to a frame. In yet another embodiment, the compression member has at least two flat plates supported by at least one tie rod. In one embodiment, the tie rods are made of rigid material and are curved. In another embodiment, the tie rods are not rigid and are bent in operation to conform to the shape of the limb around which the band is wrapped.

In one embodiment, a hemostatic device comprises three balloons wherein, after transradial access, the intraluminal pressure at the site of radial artery puncture is decreased by decompressing the distal vascular bed by occlusive compression of ipsilateral ulnar artery using inflation of a first balloon and by compressing the radial artery proximal to the puncture site using inflation of a second balloon. Subsequently, by compressing the radial artery puncture site using inflation of a third balloon, hemostasis can be achieved by applying a pressure at the puncture site that is lower in magnitude and/or duration compared to that used previously in the art to accomplish the hemostasis.

In another embodiment, hemostatic device comprises a flexible band adapted to be wrapped and secured around a hand of a patient at a site on the hand where bleeding is to be stopped, a curved plate having an inner peripheral side, which plate is made of a material more rigid than the band and at least a portion of the plate is curved toward the inner peripheral side at proximal and distal ends of the plate, a first balloon which is provided on the inner peripheral side of the curved plate near its proximal end and which inflates when a fluid is introduced therein, a first pressing member which is provided between the curved plate and the first main balloon so that at least a portion thereof overlaps with the first balloon and which is adapted for pressing against the first balloon, and a second balloon which is provided on the inner peripheral side of the curved plate near its distal end and which inflates when a fluid is introduced therein, a second pressing member which is provided between the curved plate the second main balloon so that at least a portion thereof overlaps with the second balloon and which is adapted for pressing against the second balloon.

In operation, a method of catheterization of the radial artery comprises inserting a sheath into the radial artery of a patient at an access site. The desired catheterization procedure is then performed using the sheath or catheter to access the radial artery. Once the catheterization procedure is complete, an ulnar pressure is applied to the ipsilateral ulnar artery at an ulnar pressure site while the sheath remains inserted in the radial artery. The sheath is then removed from the radial artery while maintaining the ulnar pressure to the ulnar artery. Once the sheath is removed, and while continuing to apply the ulnar pressure, pressure is applied to the radial artery at the access site to obtain hemostasis at the access site. In another embodiment, application of pressure to the radial artery at the access site to obtain hemostasis at the access site is accomplished while maintaining the ulnar pressure to the ulnar artery.

In another embodiment, vasodilator medication such as nitroglycerine is disposed on at least a portion of the skin-contacting surface of the balloon pressing on the puncture site to reduce spasm. Spasm may play a role in the process of interruption of the flow, which then leads to thrombosis and resultant lumen obliteration with fibrosis. Prevention and relief of spasm may help lower the probability of occlusion.

In yet another embodiment, a composition is disposed on at least a portion of the skin-contacting region of the balloon. The composition includes at least a hydrocolloid component and an oil component. In one embodiment, a release-coated liner is included on the skin-contacting side of the balloon. The liner is retained in place prior to use and is removed just prior to application to user's skin. The release-coated liner may be any release-coated liner known in the art that is compatible with the composition disposed on the skin-contacting side of the balloon.

BRIEF DESCRIPTION OF DRAWINGS

FIG. 1 is a schematic front view (FIG. 1A) and a schematic side view (FIG. 1B) of an embodiment of the hemostatic device 100 comprising at least two balloons 101 and 103, and a compression member that is a curved frame with rungs 104 and that is placed in a sleeve 118 formed by a covering 110 attached to a strap 108.

FIG. 2 is a schematic three-dimensional view (FIG. 2A), a schematic top view (FIG. 2B) and a schematic front view (FIG. 2C) of an embodiment of the compression member 200 that is a curved frame with rungs and comprising rungs 221 located between two curved beams 223 and 225.

FIG. 5A is a schematic top view that shows a side of the device that serves as the inside surface when the device is attached to the wrist of a patient. FIG. 5B is a schematic front view of the device.

FIG. 6A shows a schematic sectional front view of an embodiment of the hemostatic device applied on a forearm of a patient. The two balloons 601, 603 are located between the forearm of the patient and the strap 608 that goes around the forearm of the patient. FIG. 6B is a schematic sectional side view of a part of the embodiment of the hemostatic device showing balloon 603 pressing on the ulnar artery 607.

FIG. 8 is a schematic view of an embodiment of the hemostatic device wrapped around the wrist of a patient wherein FIG. 8A is an anterior view and FIG. 8B is a posterior view.

DETAILED DESCRIPTION

Figure 3:
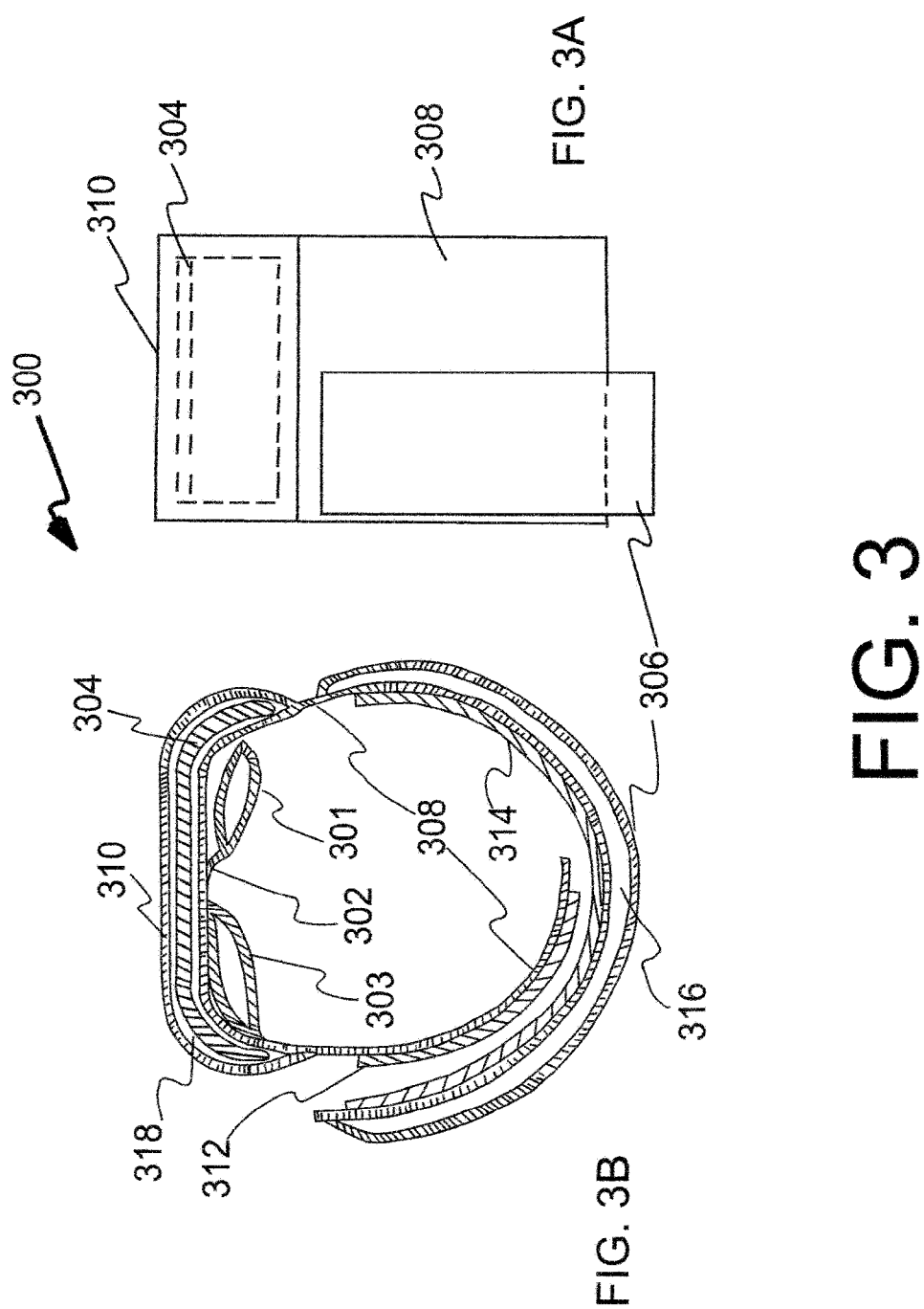
FIG. 3 is a schematic front view (FIG. 3A) and a schematic side view (FIG. 3B) of an embodiment of the hemostatic device 300 comprising at least two balloons 301 and 303, and a compression member that is a curved plate 304 and that is placed in a sleeve 318 formed by a covering 310 attached to a strap 308.

Embodiments described herein provide the user a safe, simple and reliable device and method to apply pressure at the access site of artery, e.g., radial artery to obtain hemostasis and also to apply pressure to another artery, e.g., ulnar artery using the same device.

In one embodiment of the invention (see FIG. 1), hemostatic device 100 is a flexible band comprising a flexible strap 108 adapted to be wrapped and secured by binders 112 and 114 around the wrist of a patient at a puncture site on the hand where bleeding is to be stopped, a curved frame 104, a first balloon 101, and a second balloon 103. The curved frame 104 has an inner peripheral side and is made of a material such that the frame is more rigid than the flexible strap 108. In one embodiment, the frame is made of hard plastic and substantially fixed in shape. In another embodiment, the frame is made of material (e.g. plastic) that is bendable so that the frame does not maintain a substantially fixed shape and flexes with the balloons as the balloons expand and contract with pressure. At least a portion of the frame is curved toward the inner peripheral side. The first balloon 101 is provided on the inner peripheral side at a position deviated to the center portion of the curved frame from the first end of the curved frame in lengthwise direction of the band, and the first balloon is connected to the strap 108 by a connector 102 on a side of the first balloon adjacent the center portion of the curved frame. The first balloon inflates when a fluid is introduced therein. The second balloon 103 is provided on the inner peripheral side of the curved frame at a position deviated to an edge of the curved frame from the center portion of the curved frame in widthwise direction of the band, and the second balloon is connected to the strap 108 by a connector (not shown) on a side of the second balloon adjacent the edge of the curved frame. The second balloon 103 inflates when the fluid is introduced therein. In one embodiment, the band 100 is adapted to be wrapped around the wrist with a surface fastener, e.g., Hook and Loop 112 and 114 for securing the band around the wrist. In some embodiments, pledgets (not shown) are provided for patient comfort. In one embodiment, the pledgets are made of foam.

In one embodiment, band may have a first sleeve for holding the frame 104. In the embodiment shown in FIG. 1, the first sleeve is a double layer construction formed by connecting a piece of film 110 to strap 108 of the band at a center portion of the band. The connection may be done by a suitable method such as welding (e.g., heat welding, high-frequency welding, ultrasonic welding) or adhesion/gluing (such as with an adhesive or solvent) so as to form a double layer construction. The frame 104 is inserted into a gap 118 in the double layer and thereby held. In one embodiment, in addition to the center portion of the band, at least one side end portion of the band has a sleeve. As shown in FIG. 1, band may have a second sleeve 116 at a side end portion of the band. The second sleeve is a double layer construction formed by connecting a piece of film 106 to strap 108 of the band. The connection may be done by a suitable method similar to that used for constructing the first sleeve.

The material of construction of the films or sheets used to fabricate the strap, the balloons and the sleeves of the band 100 is preferably substantially transparent whereby patient's arm can be seen through the band. Examples of the material of construction include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicones, polyurethanes various thermoplastic elastomers such as polyamide elastomers, polyurethane elastomers and polyester elastomers, and any combinations of the above in the form of, for example, resin blends, polymer alloys or laminates.

The sheet making up the band may be of any suitable thickness. In one embodiment, the thickness of the sheet material is in the range of about 0.1 to about 0.5 mm, and in some embodiments about 0.2 to about 0.3 mm. The band can be secured using hook and loop type fasteners or other suitable fasteners such as buttons, clips and buckles.

The frame 200 (see FIG. 2) is curved at both proximal and distal ends, the curvature being toward an inner peripheral side. In one embodiment, the radius of curvature $R_1$ at the proximal end is nearly the same as the radius of curvature $R_2$ at the distal end. In another embodiment, the frame is symmetrical about its center. In one embodiment, the frame is constructed of a material more rigid than the band, but maintains some flexibility whereby the frame conforms to the contour of the wrist and flexes with the expansion and contraction of balloons. In another embodiment, the frame maintains a substantially fixed shape.

In one embodiment, the frame 200 in FIG. 2 may be constructed out of material that is substantially transparent. In another embodiment, the material of construction of the frame may not be transparent. Examples of materials of construction of the frame include acrylic resins, polyvinyl chloride (rigid polyvinyl chloride and flexible polyvinyl chloride), polyolefins such as polyethylene, polypropylene and polybutadiene, polystyrene, poly(4-methyl-1-pentene), polycarbonates, ABS resins, polymethyl methacrylate (PMMA), polyacetals, polyarylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic and aliphatic polyamides, and fluorocarbon resins such as polytetrafluoroethylene. The frame may also be made of a metal or metal alloy.

The frame 200 has gaps between the rungs 221 to provide visibility of the puncture site. The rungs are held between two beams 223 and 225. The rungs and beams can have various shapes, e.g., circular, square, rectangular and elliptical. In one embodiment, the frame is entirely curved. In another embodiment, the frame is straight in the center and curved at its ends. In one embodiment, rungs 221 are circular and each rung has a diameter of about 2 mm. In another embodiment, beams 223, 225 are also circular with diameter of about 3 mm. In yet another embodiment, the gap 204 between the rungs is about 2 mm. In one embodiment, the width of the frame is about 4 mm less than the width of the strap 108 of the band 100 in FIG. 1.

In another embodiment of the invention (See FIG. 3), hemostatic device comprises a flexible band 300. The band has a flexible strap 308 having an inner peripheral side and adapted to be wrapped and secured using binders 312 and 314 around a limb of a patient at a site on the limb where bleeding is to be stopped, a plate 304 made of a material more rigid than the band and at least a portion of the plate is curved toward its inner peripheral side at proximal and distal ends of the plate. In one embodiment, the plate 304 is of substantially fixed shape. In another embodiment, the plate 304 is flexible and does not maintain a substantially fixed shape. The material of construction of plate 304 is same as material of construction of frame 200 discussed before. In one embodiment, the plate 304 is placed in a sleeve 318 formed by a covering 310 attached to the strap 308 on the outer peripheral side of the strap at a center portion of the band. In another embodiment, both the covering 310 and the strap 308 are made of flexible plastic and are transparent. The covering 310 can be attached to strap 308 using known techniques, for example ultrasonic welding. In one embodiment, in addition to the center portion of the band, at least one side end portion of the band has a sleeve 316. The sleeve at a side end portion of the band may also be a double layer construction formed by connecting a piece of film 306 to strap 308 on the outer peripheral side of the strap 308. The connection may be done by a suitable method similar to that used for constructing the sleeve at center portion of the band. The plastic sheet material used to make the strap of the band could also be used to make the sleeves.

The first balloon 301 is provided on the inner peripheral side at a position deviated to the center portion of the curved plate from the first end of the curved plate in lengthwise direction of the band, and the first balloon is connected to the strap 308 by a connector 302 on a side of the first balloon adjacent the center portion of the curved plate. The first balloon inflates when a fluid is introduced therein. The second balloon 303 is provided on the inner peripheral side of the curved plate at a position deviated to an edge of the curved plate from the center portion of the curved plate in widthwise direction of the band, and the second balloon is connected to the strap 308 by a connector (not shown) on a side of the second balloon adjacent the edge of the curved plate. The second balloon 303 inflates when the fluid is introduced therein. In one embodiment, the band 300 is adapted to be wrapped around the wrist with a surface fastener, e.g., Hook and Loop 312 and 314 for securing the band around the wrist.

Figure 4:
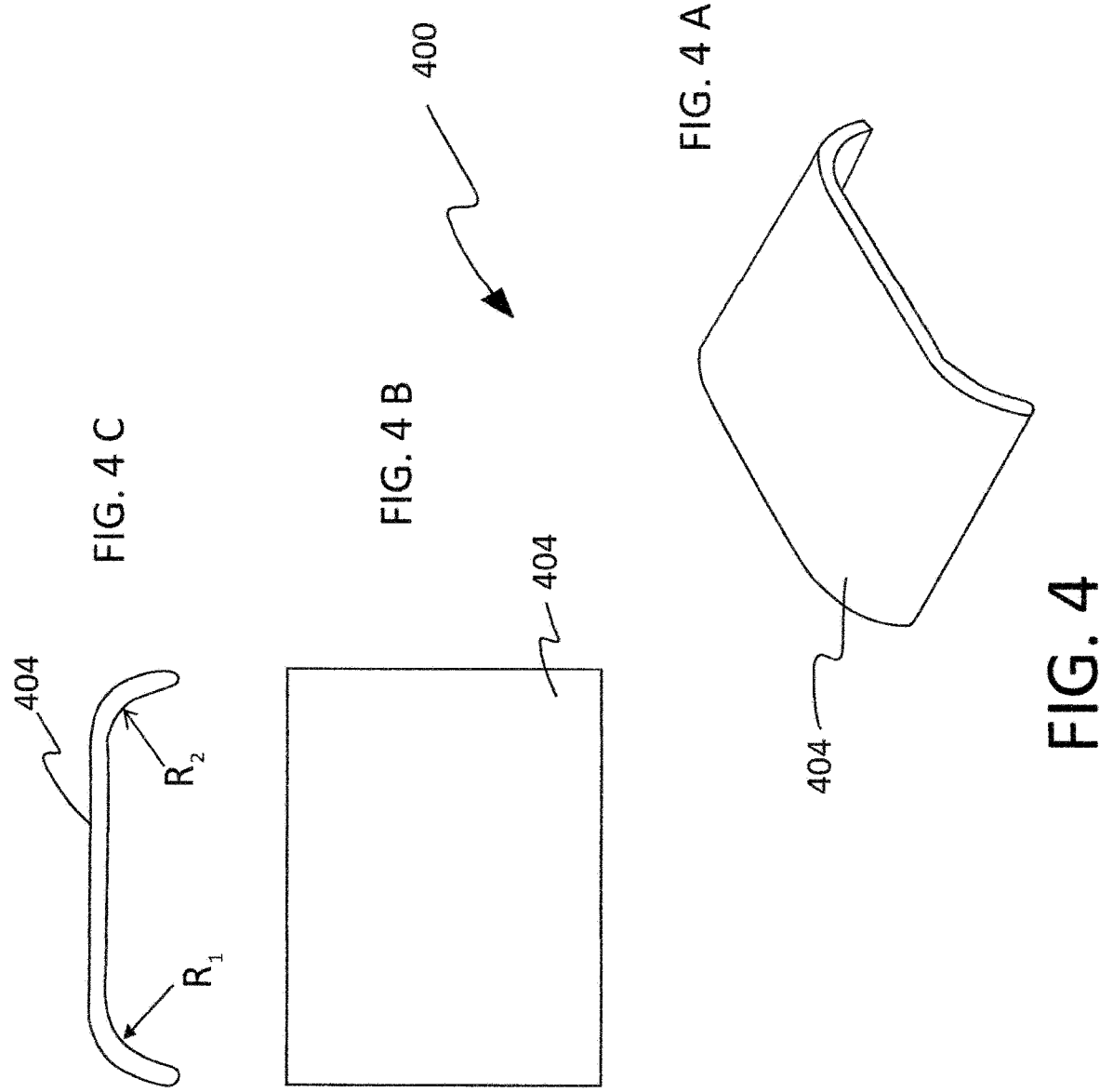
FIG. 4 is a schematic three-dimensional view (FIG. 4A), a schematic top view (FIG. 4B) and a schematic front view (FIG. 4C) of an embodiment of the compression member 400 that is a curved plate.

The plate 400 (see FIG. 4) is curved at both proximal and distal ends, the curvature being toward an inner peripheral side. In one embodiment, the radius of curvature $R_1$ at the proximal end is nearly the same as the radius of curvature $R_2$ at the distal end. In another embodiment, the plate 404 is symmetrical about its center. In one embodiment, the plate is constructed of a material more rigid than the band, but maintains some flexibility whereby the plate conforms to the contour of the wrist and flexes with the expansion and contraction of balloons. In another embodiment, the plate maintains a substantially fixed shape. The plate 400 may be constructed using same materials as used to construct frame 200 in FIG. 2. In one embodiment, the thickness of plate is about 2 mm. The width of the plate may be about 4 mm less than the width of the strap of the band, thereby keeping on either side of the plate a gap of about 2 mm between the edge of the plate and the edge of the strap of the band.

In another embodiment of the invention (See FIG. 5), hemostatic device 500 comprises a flexible band. The band has a flexible strap 508 having an inner peripheral side and adapted to be wrapped and secured using binders 512 and 514 around a limb of a patient at a site on the limb where bleeding is to be stopped. The band has a center portion and two side portions on either side of the center portion. In one embodiment, the center portion has a first sleeve 518 formed by a covering 510 attached to strap 508. A compression member (not shown) is placed in the first sleeve 518. In one embodiment, the compression member is a curved frame (see FIG. 2). In another embodiment, the compression member is a curved plate (see FIG. 4). In one embodiment, both the covering 510 and the strap 508 are made of flexible plastic and are transparent. The covering 510 can be attached to strap 508 using known techniques, for example ultrasonic welding. A first balloon 501 is provided on the inner peripheral side at a position deviated to the center portion of the first sleeve 518 from the proximal end of the first sleeve in lengthwise direction of the band, and the first balloon is connected to the strap 508 of the band by a connector 502 on a side of the first balloon adjacent the center portion of the first sleeve 518. In one embodiment, the width of the first balloon is nearly the same as the width of the strap 508 of the band, and the length of the first balloon is about half the length of the first sleeve 518. The first balloon 501 inflates when a fluid is introduced therein. The second balloon 503 is provided on the inner peripheral side of the first sleeve 518 at a position deviated to an edge of the first sleeve from the center portion of the first sleeve in widthwise direction of the band, and the second balloon is connected to the strap 508 of the band by a connector 504 on a side of the second balloon adjacent an edge of the first sleeve 518. The width of the second balloon is about half the width of the strap 508 of the band and the length of the second balloon is about half the length of the first sleeve 518. In another embodiment, the width of the second balloon is about 70% of the width of the band. In yet another embodiment, the width of the second balloon is about 60% of the width of the band. In a further embodiment, the width of the second balloon is about 50% of the width of the band. The second balloon 503 inflates when the fluid is introduced therein.

The material of construction of the balloons is preferably transparent and may be the same as used to make the band. In one embodiment, the material of construction of the balloon could be sheets of thickness similar to that used to make the strap of the band. In another embodiment, the sheets used to make balloons could be thinner than the sheets used to make the strap of the band. In one embodiment, the strap is made of polyvinyl chloride film of thickness 20 mils (0.508 mm) and a balloon is made of polyvinyl chloride film of thickness 10 mils (0.254 mm). The balloons could have any shape such as square, rectangular, circular and elliptical. The balloons can be made by sealing sheet cut to appropriate shape and sealed at the edge using sealing technique such as adhesion or welding. The balloons are connected to the band by flexible connectors 502 and 504 that could be made of same material as the balloon and the band. In one embodiment, the band and the compression member are substantially transparent. In another embodiment, the balloon 503 is made of translucent or opaque material and the balloon 501 is made of substantially transparent material.

Figure 5:
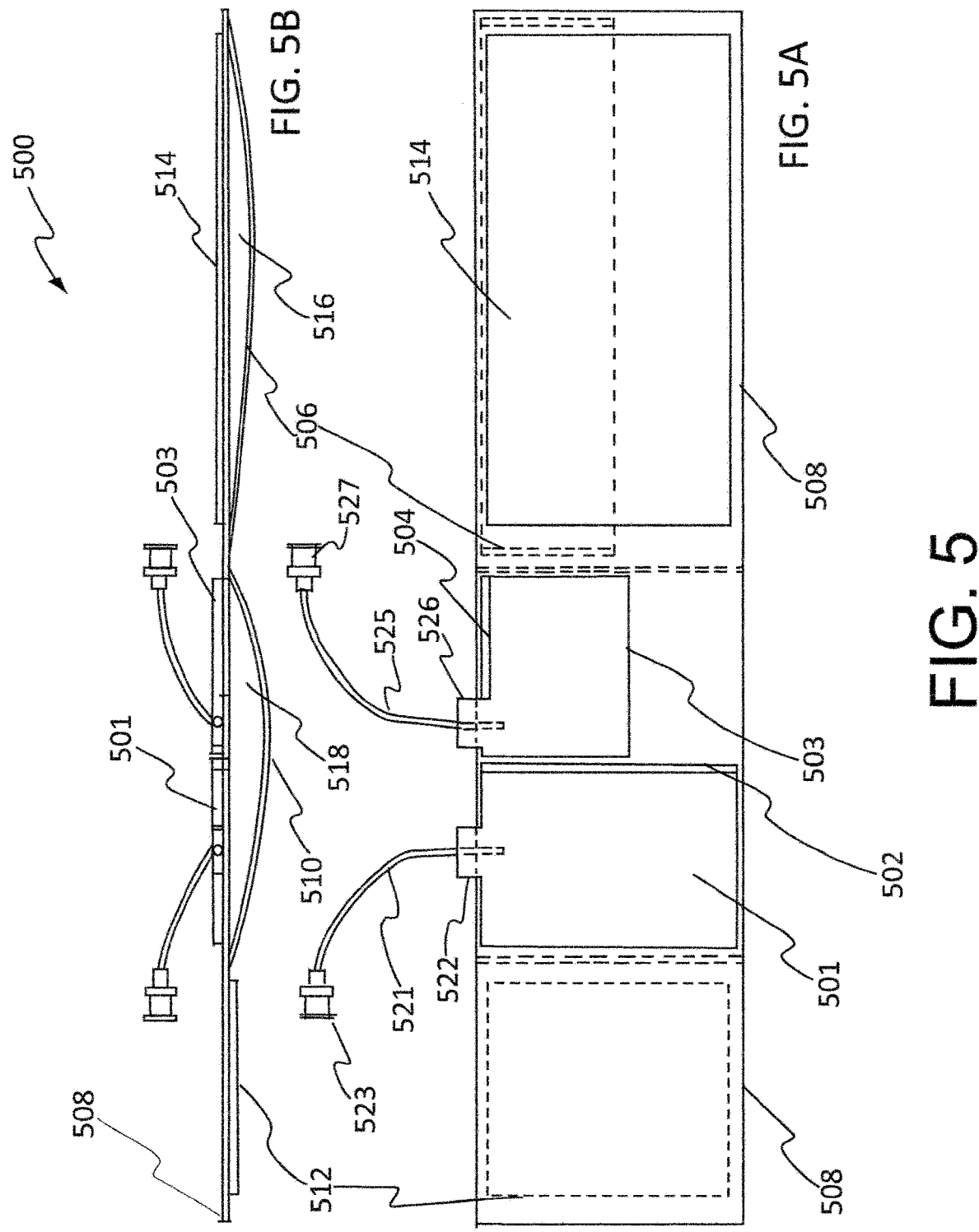
FIG. 5 is a schematic view of hemostatic device 500 with two balloons 501 and 503.

As shown in FIG. 5, the first balloon 501 has connected thereto a tube 521 for introducing a fluid into the first balloon, and the second balloon 503 has connected thereto a tube 525 for introducing a fluid into the second balloon. In one embodiment, the tubes are transparent and flexible. Tube 521 is connected at a proximal end thereof to the first balloon 501 at 522. Tube 525 is connected at a proximal end thereof to the second balloon 503 at 526. Tube 521 may include an adapter 523 that is connected to the distal side of the tube, and tube 525 may include an adapter 527 that is connected to the distal side of the tube. In one embodiment, adapter 523 is identifiably different from adapter 527 so that a user knows to select the appropriate adapter that connects to the balloon user wants to inflate. The identifiable differentiation of the adapters may be through visual distinction comprising color, shape, texture or combination thereof. Inflation of the balloon is carried out by inserting the protruding tip of a syringe (not shown) into the adapter and pushing a plunger on the syringe so as to introduce fluid within the syringe through the inflator into the balloon. Once fluid has been injected into the balloon and the protruding tip of the syringe is withdrawn from the adapter, a check valve within the adapter closes, preventing the fluid from leaking out and thus maintaining the balloon in an inflated state. In another embodiment, a two-way or three-way valve is used to direct the flow of fluid into and out of the balloon, and to prevent the fluid from leaking out and thus maintaining the balloon in an inflated state.

In one embodiment, in addition to the center portion of the band, at least one side end portion of the band has a sleeve. As shown in FIG. 5, the band may have a second sleeve 516 at one side end portion of the band. The second sleeve is a double layer construction formed by connecting a piece of film 506 to strap 508 of the band. The connection may be done by a suitable method similar to that used for constructing the first sleeve. The second sleeve 516 may be used to hold tubes 521, 525 and adapters 523, 527 when the band is wrapped around the wrist of a patient (See FIG. 8).

The technique of providing a compression member on the band is not limited to the illustrated arrangement and may involve joining the compression member(s) to the inside surface or outside surface of the band by a suitable method such as welding or adhesion. It is not necessary that the band encircle the limb, e.g., wrist completely. For example, another arrangement may be the band is held in place by tie down that holds the band firmly on the wrist. In another embodiment, the band does not have any compression member to enhance rigidity.

Figure 6:
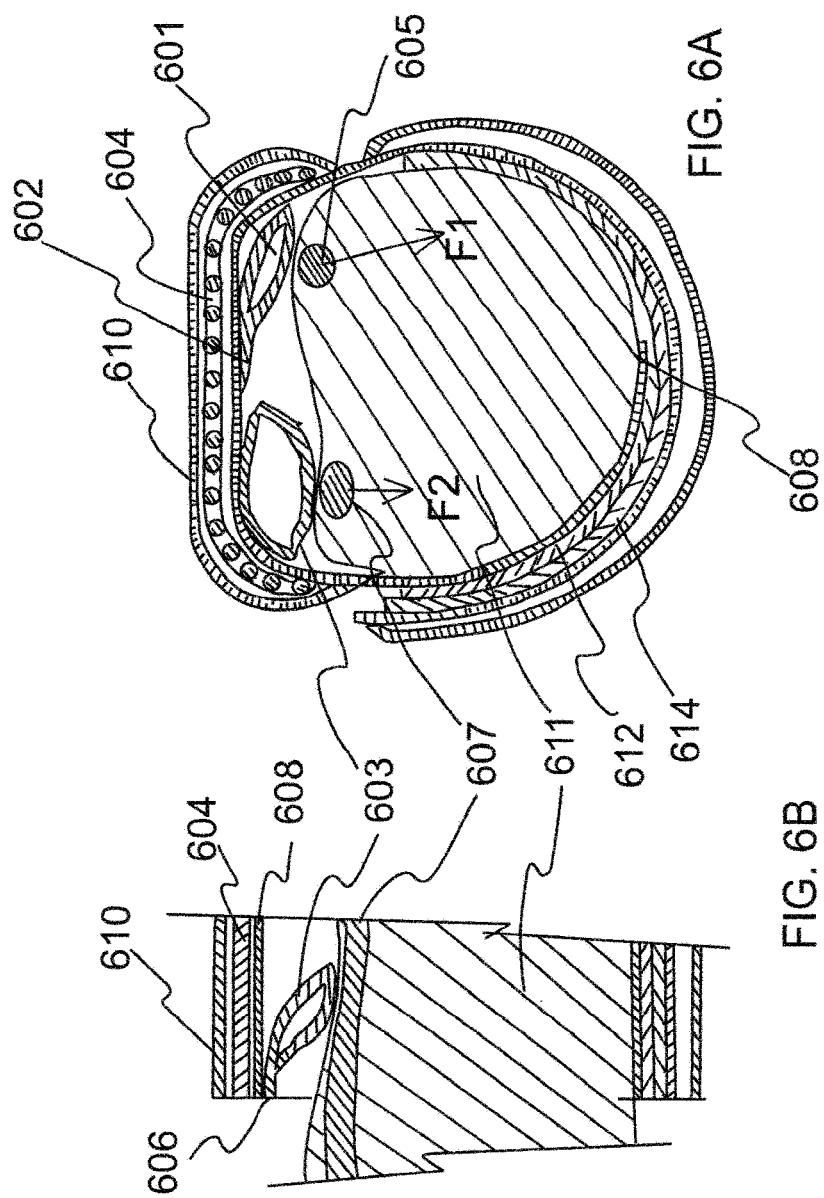
FIG. 6 is schematic sectional view showing hemostatic device of FIG. 1 in use.

FIG. 6 is a sectional view showing a band in a wrapped state to the wrist 611. The band is attached to the wrist by connecting together surface fasteners (e.g. hook and loop fasteners) 612 and 614. Other means for securing the band in a wrapped state around the wrist include buttons, clips, snaps, zippers, and buckles through which the ends of the band pass. A frame 604 is placed in a sleeve formed by a covering 610 attached to the strap 608 on the outer peripheral side of the strap at a center portion of the band. One side of balloon 601 is connected to the strap 608 of the band by connector 602 at a position deviated to the center portion of the curved frame 604 from the end of the curved frame in lengthwise direction of the band. As a result, the balloon assumes an orientation whereby the pressing force F1 applied to the puncture site on the radial artery 605 acts generally in an outward direction away from the center portion of the wrist (See FIG. 6A). Consequently, force F1 does not have an impact at the location of the ulnar artery 607. On the other hand, if the balloon 601 was connected to the band at a position deviated to the end of the curved frame, the balloon would assume an orientation whereby the pressing force would be in an oblique direction towards the center portion of the wrist whereby a component of the force F1 would affect the ulnar artery 607.

The ulnar artery 607 is compressed by balloon 603, which is provided on the inner peripheral side of the curved frame 604 at a position deviated to an edge of the curved frame from the center portion of the curved frame in widthwise direction of the band, and balloon 603 is connected to the band by a connector 606 on a side of balloon 603 adjacent to an edge of the curved frame 604 (see FIG. 6B). In the present embodiment where one side of balloon 603 is connected by a connector at an edge of the band and the width of the balloon 603 is shorter than the width of the strap 608, balloon 603 assumes an orientation whereby component of the force F2 in the cross-sectional plane of the wrist is generally vertical (see FIG. 6A). The force F2 may have a component in a direction towards the elbow, but a negligible component in a direction towards the radial artery. Therefore, operation of balloon 603 to pressurize or depressurize the ulnar artery will not generally affect operation of balloon 601 to pressurize or depressurize the radial artery, and vice versa.

Figure 7:
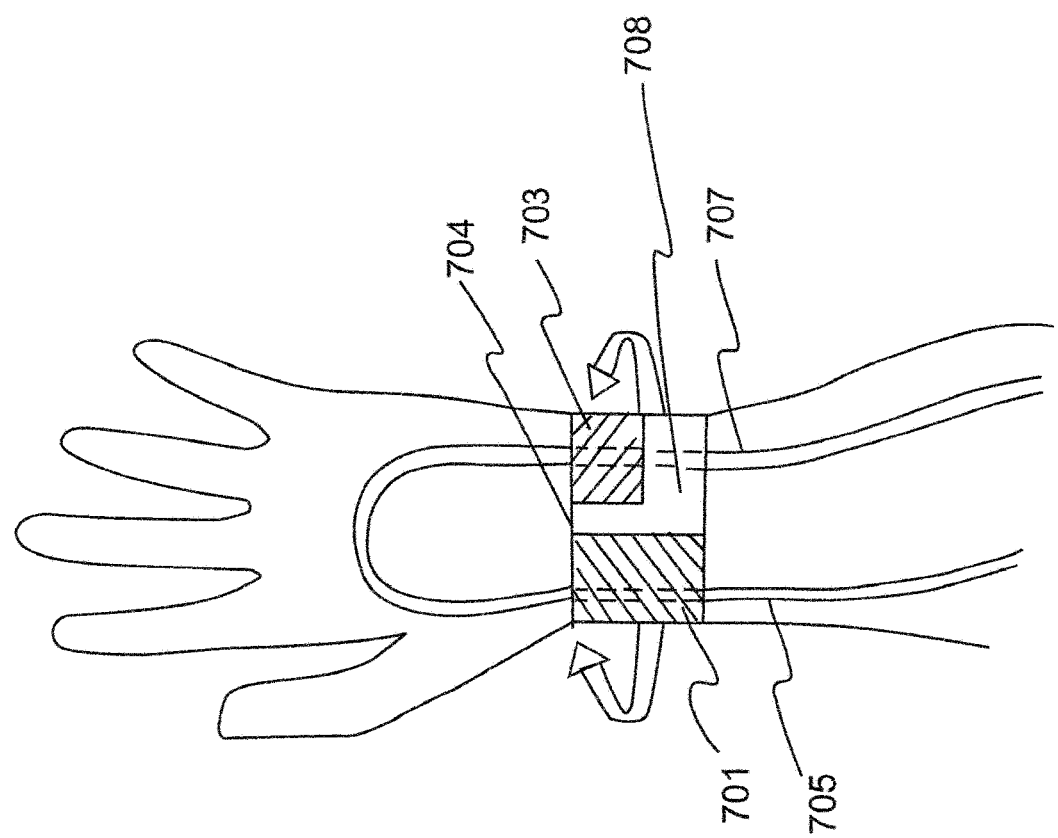
FIG. 7 is a schematic view of an embodiment of the hemostatic device showing placement of balloon 701 over radial artery 705 and balloon 703 over ulnar artery 707.

FIG. 7 is a schematic of a band 708 wrapped around a wrist whereby balloon 701 compresses the radial artery 705 and balloon 703 compresses the ulnar artery 707. In the embodiment in FIG. 7, the balloon 703 is located at or near the base of the palm (Guyon's canal) 704 thereby compressing the ulnar artery 707 at a location where it is most accessible for compression and the balloon 701 is located over the puncture site, which is generally about 2 cm. from the base of a palm. The pressure applied to the radial artery and the ulnar artery could be simultaneously and independently manipulated to optimize the pressure at which the bleeding from the radial artery stops while at the same time a high enough pressure is applied to the ulnar artery to prevent or minimize occlusion of the radial artery. In one embodiment, mark or marks (not shown) may be placed on the radial balloon 701 to help a user visually place a central portion of the radial balloon 701 on the radial artery 705 at or near the puncture site of the artery. Mark or marks may also be placed on the compression member and the sleeve holding the compression member to help a user in the placement of the radial balloon 701 on the puncture site. Mark may be a dot, a line, a square, a triangle or any other shape that helps in the placement.

Figure 8:
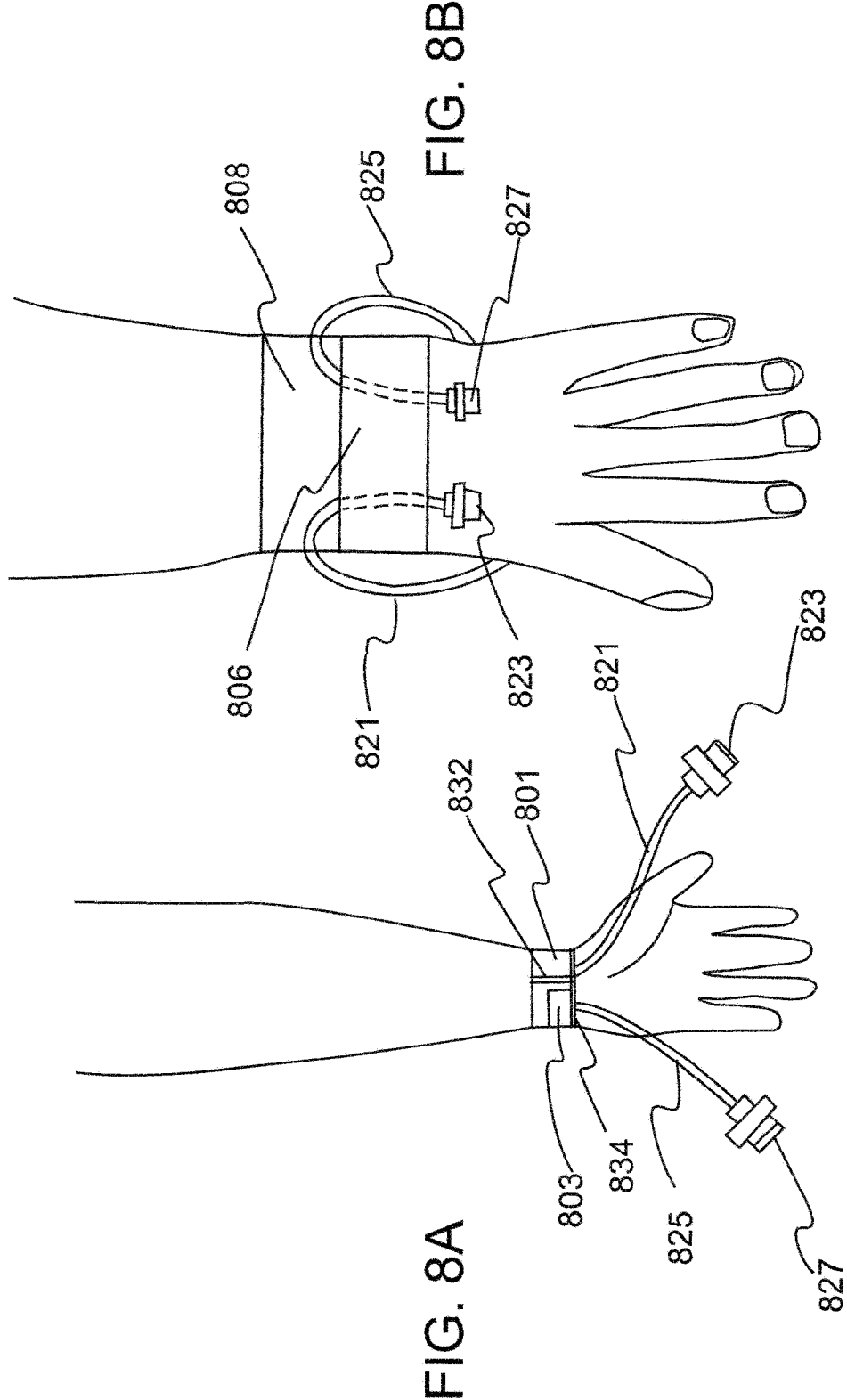

FIG. 8 is a schematic illustration showing an anterior view (FIG. 8A) and a posterior view (FIG. 8B) of an embodiment of a band 808 wrapped around the wrist of a patient. One side of radial balloon 801 is connected to the band by connector 832 such that the connector 832 is positioned towards the center portion of the wrist. The radial balloon 801 is inflated or deflated by passing fluid (a gas such as air or a liquid such as saline) through tube 821 using a syringe (not shown) that is connected to adapter 823. The ulnar balloon 803 is inflated or deflated by passing fluid (a gas such as air or a liquid such as saline) through tube 825 using a syringe (not shown) that is connected to adapter 827. A balloon will inflate when a fluid is introduced therein, thereby applying pressure to the skin of the patient where the balloon is located. In one embodiment, the fluid is introduced using a syringe. The syringe may have markers to determine the amount of fluid that will be inserted into a balloon. The syringe may also have an outlet that can be connected to a pressure measuring device such as a manometer. In another embodiment, the balloons may have an outlet that can be connected to a pressure measuring device. The pressure measurement helps the user to inflate the balloon to a pressure that is not significantly higher than the systolic pressure of the patient, thereby allowing robust hemostasis but preventing grossly excessive compression by inordinate pressure, thereby lowering the probability of lumen compression to the point of occlusion, and flow cessation.

The edge of the band is positioned close to the base of the palm 834. The band 808 may have a sleeve 806 at a side end portion of the band. The sleeve is a double layer construction and tubes 821, 825 and adapters 823 and 827 may be inserted in the sleeve 806 so that the tubes do not dangle when a patient moves his/her hand.

Figure 9:
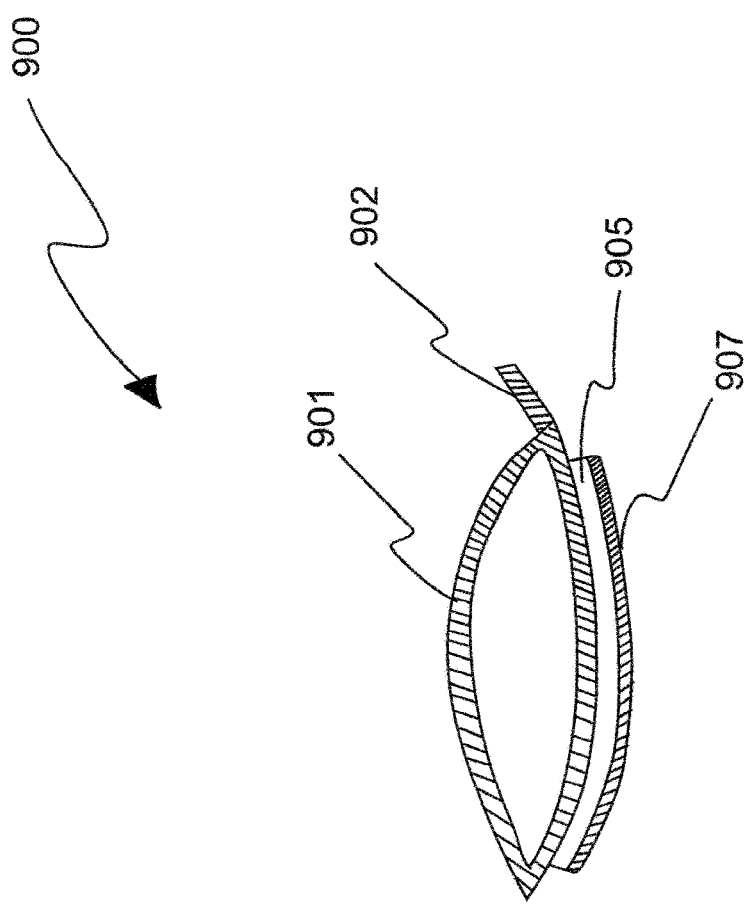
FIG. 9 is a schematic view of a balloon 900 wherein a surface of the balloon to be in contact with skin is disposed with a composition 905 and a liner 907.

FIG. 9 shows an embodiment of balloon 900 where the surface of the balloon 901 in contact with skin is coated with a composition 905. In one embodiment, composition 905 may comprise a hydrocolloid adhesive or zinc oxide-based adhesive that can be advantageously used upon the surface of the balloon when pressing the balloon on the skin of the patient. The hydrocolloid or zinc oxide-based adhesive can be used either alone or in combination with another medical grade adhesive. Hydrocolloid and zinc oxide-based adhesives have less of a tendency to excoriate the skin of a patient when removed. This can be particularly important for patients whose skin is more sensitive or fragile. In one embodiment, the coated composition 905 has a peel-off laminate (liner) 907 that is removed before placing the balloon on the puncture site. In another embodiment, the composition also contains antimicrobials. In one embodiment, the composition contains oil. Such compositions are known in the art and commercially available. See, e.g., compositions and laminates sold by Vancive Medical Technologies, Avery Dennison business. In some embodiments, connector 902 may be provided to connect the balloon to the band. In another embodiment, vasodilator medication is present on the surface of a balloon pressing on the puncture site to reduce spasm. Spasm is thought to play a role in the process of interruption of the flow that then leads to thrombosis and resultant lumen obliteration with fibrosis. Prevention and relief of spasm may help lower the probability of occlusion. An example of such vasodilator medication is nitroglycerine. In one embodiment, the surface of balloon in contact with the puncture site is disposed with nitroglycerine.

Figure 10:
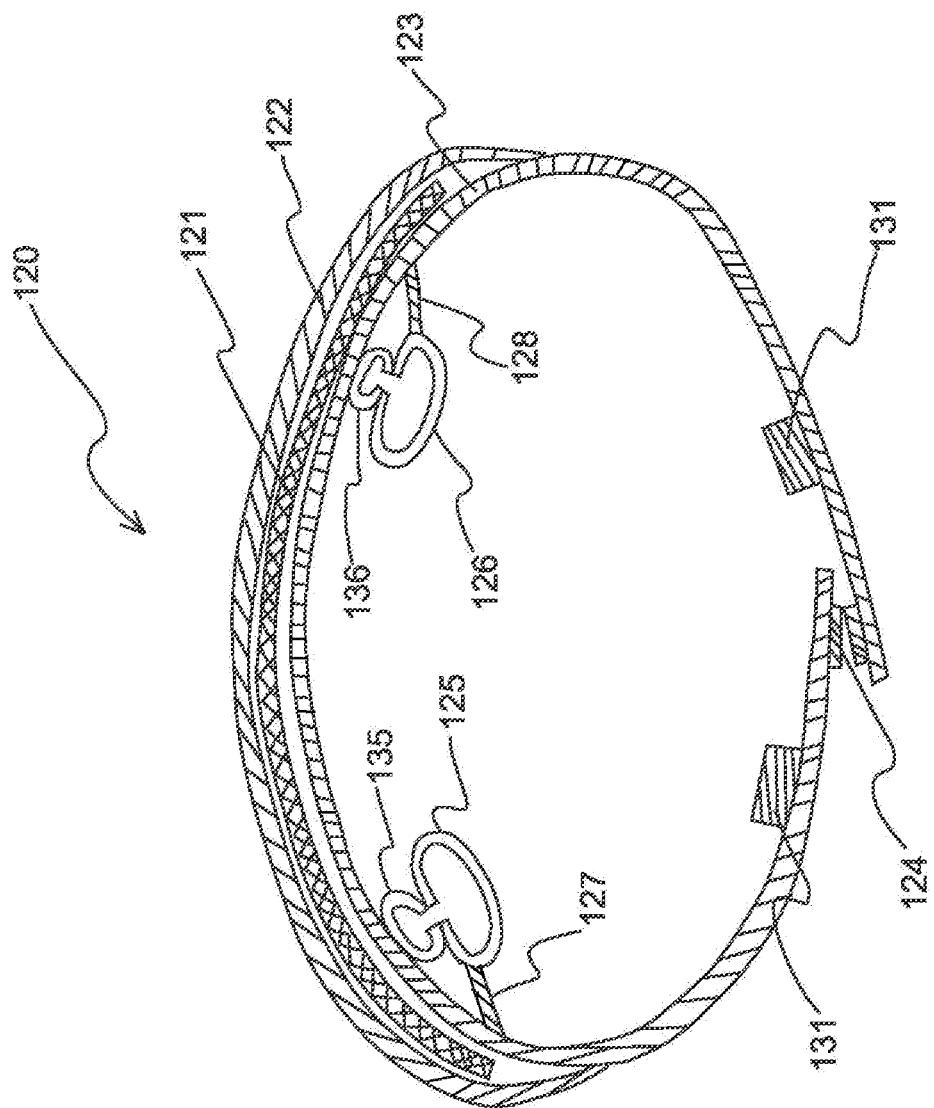
FIG. 10 is a schematic side view of an embodiment of the hemostatic device comprising two primary balloons 125, 126, two auxiliary balloons 135, 136 and a compression member 121 that is placed in a sleeve formed by a covering 122 attached to a band 123.

In another embodiment of the invention (See FIG. 10), hemostatic device comprises a flexible band 120. The band has a flexible strap 123 having an inner peripheral side and adapted to be wrapped and secured using binders 124 around a limb of a patient at a site on the limb where bleeding is to be stopped, a compression member 121 having an inner peripheral side, which compression member is made of a material more rigid than the band and at least a portion of the compression member is curved toward its inner peripheral side at proximal and distal ends of the compression member. In one embodiment, the compression member 121 is placed in a sleeve formed by a covering 122 attached to the strap 123. In another embodiment, both the covering 122 and the strap 123 are made of flexible plastic and are transparent. The covering 122 can be attached to strap 123 using known techniques, for example ultrasonic welding. A first balloon 125 which is provided on the inner peripheral side of the strap near the proximal end of the sleeve and which inflates when a fluid is introduced therein, and a second balloon 126 which is provided on the inner peripheral side of the strap near the distal end of the sleeve and which inflates when a fluid is introduced therein. Two auxiliary balloons 135 and 136 are provided. Auxiliary balloon 135 is communicably connected to the first balloon 125, and auxiliary balloon 136 is communicably connected to the second balloon 126. In another embodiment, at least the first or the second balloon is communicably connected to corresponding pressing member.

In another embodiment, the band and the compression member are substantially transparent. In yet another embodiment, at least the first or the second balloon is connected to the band using connectors 127 and 128. In another embodiment, pledgets 131 are provided for patient comfort. In one embodiment, the pledgets are made of foam.

The method of providing compression member on the band is not limited to the illustrated arrangement and may involve joining the compression member(s) to the inside surface or outside surface of the band by a suitable method such as welding or adhesion. It is not necessary that the band encircle the limb, e.g., wrist completely. For example, another arrangement may be the band is held in place by tie down that holds the band firmly on the wrist. In another embodiment, the band does not have any compression member to enhance rigidity.

Figure 11:
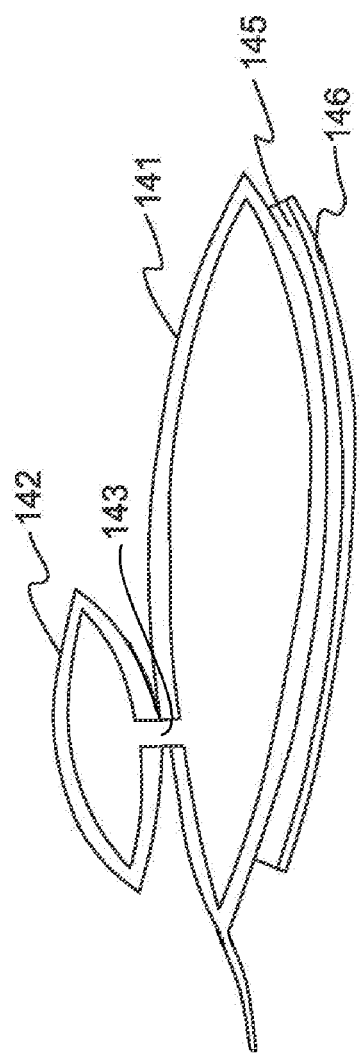
FIG. 11 is a schematic view of a primary balloon 141, auxiliary balloon 142, wherein the balloon surface of primary balloon to be in contact with skin is disposed with a composition 145 and a liner 146.

FIG. 11 shows a primary balloon 141 communicably connected through channel 143 to auxiliary balloon 142. In one embodiment, the surface of the balloon 141 in contact with skin is coated with a composition 145. In one embodiment, the coated composition 145 has a peel-off laminate (liner) 146 that is removed before placing the balloon on the puncture site. In one embodiment, the composition is a hydrocolloid. In another embodiment, the composition also contains antimicrobials. In one embodiment, the composition contains oil. Such compositions are known in the art and commercially available. See, e.g., compositions and laminates sold by Vancive Avery Dennison.

Figure 12:
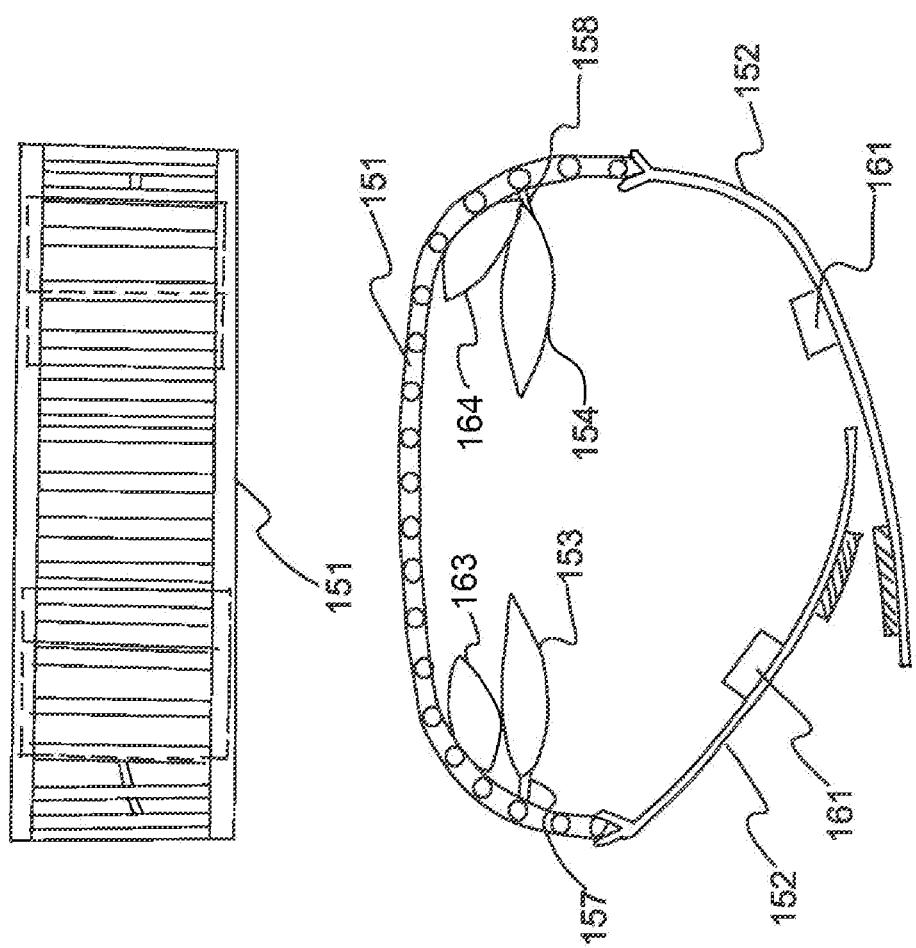
FIG. 12 is a schematic view of an embodiment of the hemostatic device comprising a frame 151 and ties 152 to tie the frame to the forearm, wherein balloons 153, 154 are connected to the frame.

In another embodiment, band 152 is connected to both ends of a frame 151 (see FIG. 12). The frame has connected to the inner side thereof balloons 153 and 154 made of a flexible material. The balloons inflate when a fluid (a gas such as air, or a liquid such as saline) is introduced therein, thus applying pressure on the radial and ulnar arteries. In one embodiment, two pairs of balloons are positioned near two ends of the frame. The material of construction of the balloons is preferably transparent and may be the same as used to make the band. The material of construction of the balloon could be sheets of thickness similar to that used to make the band. The balloons could have any shape such as square, rectangular, circular and elliptical. The balloons can be made by sealing sheet cut to appropriate shape and sealed at the edge using sealing technique such as adhesion or welding. The balloon is connected to the frame by flexible connectors 157 and 158 which could be made of same material as the balloon and the band.

As shown in FIG. 12, auxiliary balloons 163 and 164 composed of a flexible material may be provided between the frame and the primary balloon in such a way that all or part of the auxiliary balloon overlaps with the main balloon. This auxiliary balloon functions as a pressing member for pressing against the main balloon. The material making up the auxiliary balloon could be similar to the materials making up the band and the primary balloon. It is preferable for the auxiliary balloon to be substantially transparent to ensure that the puncture site is externally visible. The material making up the auxiliary balloon is in the form of a sheet which may have a thickness like that of the material making up the primary balloon. The auxiliary balloon may also have a construction like that of the primary balloon.

In one embodiment, the secondary balloon has a smaller width in the lengthwise direction of the band than the main balloon. Hence, the secondary balloon is smaller in size than the main balloon and thus applies pressure locally to the main balloon. In another embodiment, pledgets 161 are provided for patient comfort. In one embodiment, the pledgets are made of foam.

Figure 13:
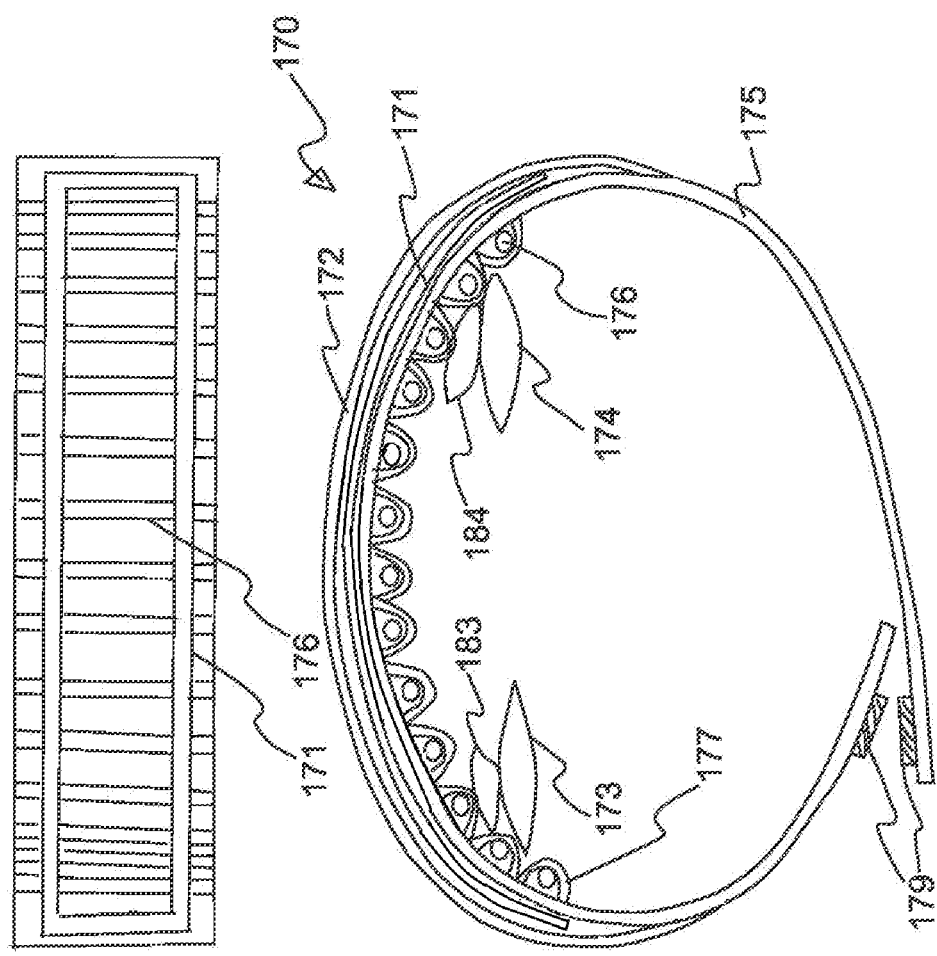
FIG. 13 is a schematic view of an embodiment of the hemostatic device comprising rods 176 placed in pockets 177 and a frame 171 placed in a sleeve and the balloons 173, 183, 174, 184 are underneath the rods.

In another embodiment of the invention (See FIG. 13), hemostatic device comprises a flexible band 170. The band has a flexible strap 175 having an inner peripheral side and adapted to be wrapped and secured using binders 179 around a limb of a patient at a site on the limb where bleeding is to be stopped, a frame 171 made of a material more rigid than the band and at least a portion of the frame is curved toward its inner peripheral side at proximal and distal ends of the compression member. In one embodiment, the frame 171 is of substantially fixed shape. In another embodiment, the frame 171 is flexible. The material of construction of frame 171 is same as material of construction of frames discussed before. In one embodiment, the frame 171 is placed in a sleeve formed by a covering 172 attached to the strap 175 on the outer peripheral side of the strap. In another embodiment, both the covering 172 and the strap 175 are made of flexible plastic and are transparent. The covering 172 can be attached to strap 175 using known techniques, for example ultrasonic welding. In one embodiment, on the inner peripheral side of the strap, a number of pockets 177 are formed using flexible, transparent plastic material. The plastic sheet material used to make the strap of the band could also be used to make the pockets. The pockets are attached to strap 175 using known techniques, for example ultrasonic welding. Rods 176 are placed in these pockets. In one embodiment, the diameter of the rods 176 is in the range of 2 to 4 mm. In another embodiment, the material of construction of rods is rigid, transparent plastic. In another embodiment, flat planks may be placed in the pockets. In yet another embodiment, a combination of rods and planks may be placed in the pockets. The frame 171 is less rigid than the rods 176, but more rigid than the strap 175. A first balloon 173 which is provided on the inner peripheral side of the strap near the proximal end of the sleeve and which inflates when a fluid is introduced therein, and a second balloon 174 which is provided on the inner peripheral side of the strap near the distal end of the sleeve and which inflates when a fluid is introduced therein. Two auxiliary balloons 183 and 184 are provided. Auxiliary balloon 183 is communicably connected to the first balloon 173, and auxiliary balloon 184 is communicably connected to the second balloon 174.

Figure 14:
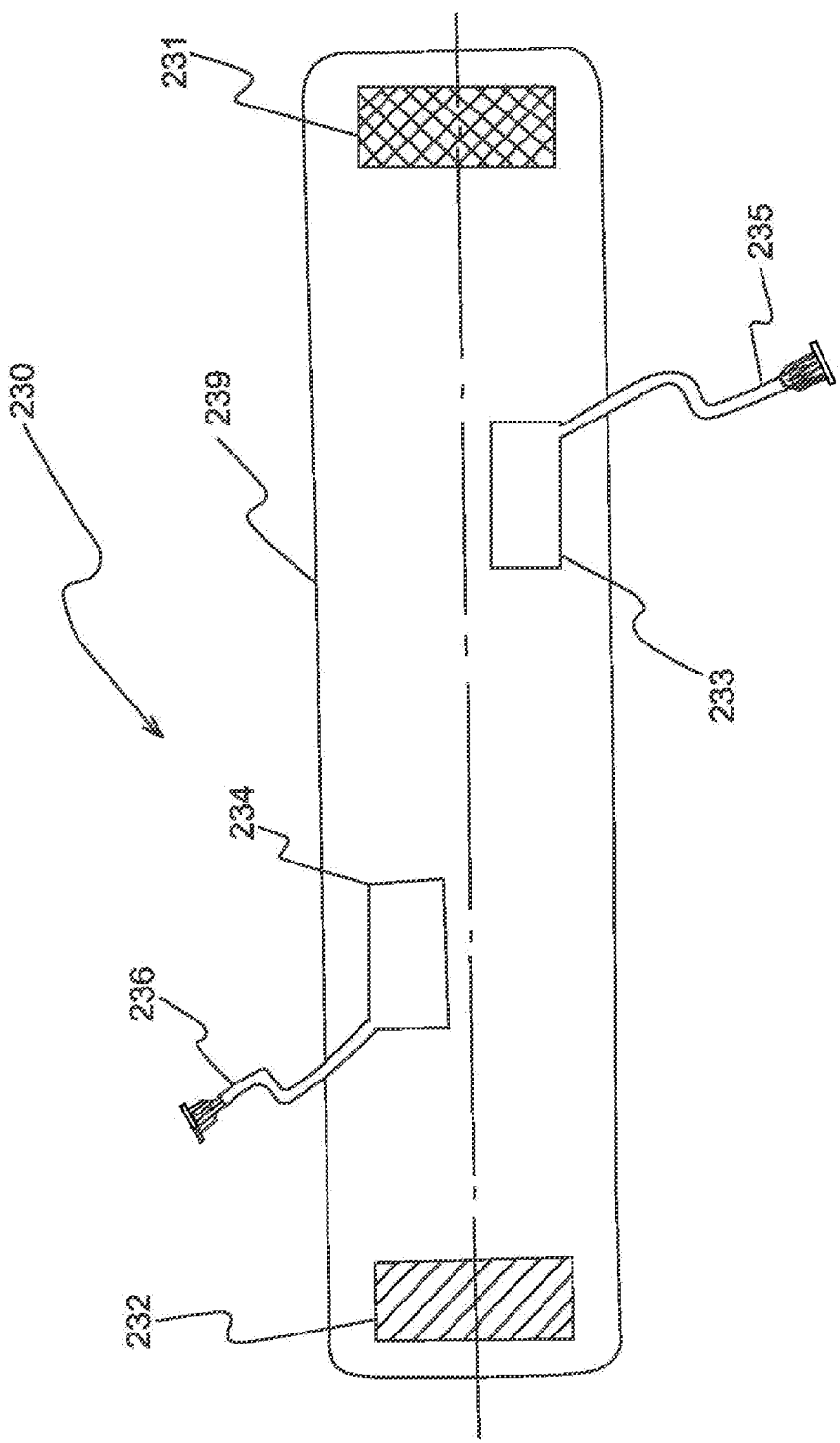
FIG. 14 is a bottom view of an embodiment of the hemostatic device comprising at least two balloons. This shows the side of the device that serves as the inside surface when the device is attached to the wrist of a patient.

In one embodiment of the invention (see FIG. 14), hemostatic device 230 comprises a flexible band 239 adapted to be wrapped and secured by binders 231, 232 around the hand of a patient at a site on the hand where bleeding is to be stopped, a first balloon 233 which is provided on the inner peripheral side of the band near the proximal end and which inflates when a fluid is introduced therein using a tube 235, and a second balloon 234 which is provided on the inner peripheral side of the band near the distal end and which inflates when a fluid is introduced therein using tube 236. The balloons may be connected to the band using connectors (not shown).

Figure 15:
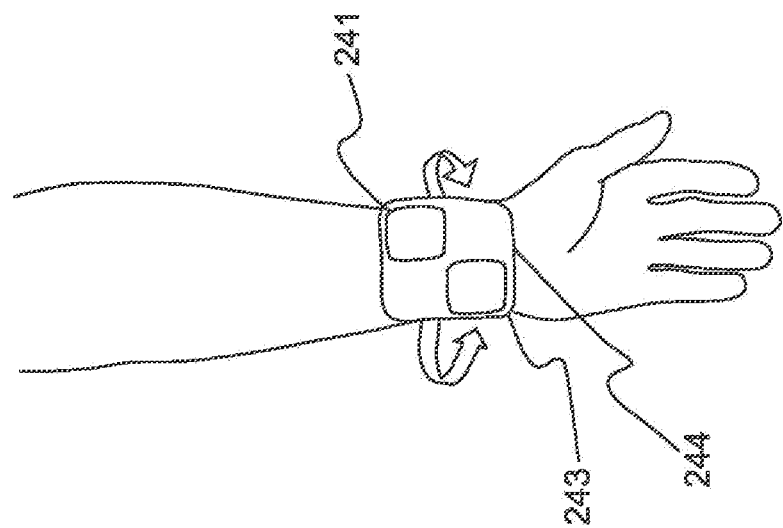
FIG. 15 is a schematic view of an embodiment of the hemostatic device applied on a forearm of a patient. The two balloons 241, 243 are located between the forearm of the patient and the band 244 that goes around the forearm of the patient.

FIG. 15 is a schematic of a band 244 wrapped around a wrist whereby balloon 241 compresses the radial artery and balloon 243 compresses the ulnar artery. In the embodiment in FIG. 15, the first balloon is located at the base of the palm (Guyon's canal) thereby compressing the ulnar artery at a location where it is most accessible for compression and the second balloon is located at the puncture site which is generally about 2 cm. from the base of a palm. The center of the first balloon and the center of the second balloon are offset from each other, and the two balloons are located on either side of the line of axis of the band. In another embodiment, the two balloons are located on the line of axis of the band. In yet another embodiment, the first balloon is larger than the second balloon. The pressure applied to the radial artery and the ulnar artery could be simultaneously and independently manipulated to optimize the pressure at which the bleeding from the radial artery stops while at the same time a high enough pressure is applied to the ulnar artery to prevent or minimize occlusion of the radial artery.

Figure 16:
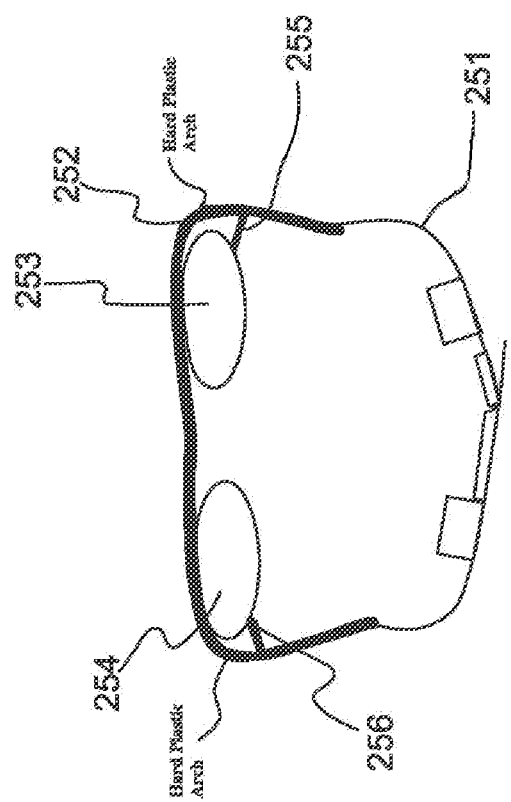
FIG. 16 is a schematic side view of an embodiment of the hemostatic device comprising a hard plastic compression member 252 and two balloons 253, 254 configured to compress two different arteries with parallel course.

In another embodiment of the invention (see FIG. 16), hemostatic device comprises a flexible band 251 adapted to be wrapped and secured around the hand of a patient at a site on the hand where bleeding is to be stopped, a compression member 252 having an inner peripheral side, which member is made of a material more rigid than the band and at least a portion of the member is curved toward the inner peripheral side at proximal and distal ends of the member, and a first balloon 253 which is provided on the inner peripheral side of the compression member near the proximal end and which inflates when a fluid is introduced therein, and a second balloon 254 which is provided on the inner peripheral side of the compression member near the distal end and which inflates when a fluid is introduced therein. The balloons may be connected to the band using connectors 255 and 256.

Figure 17:
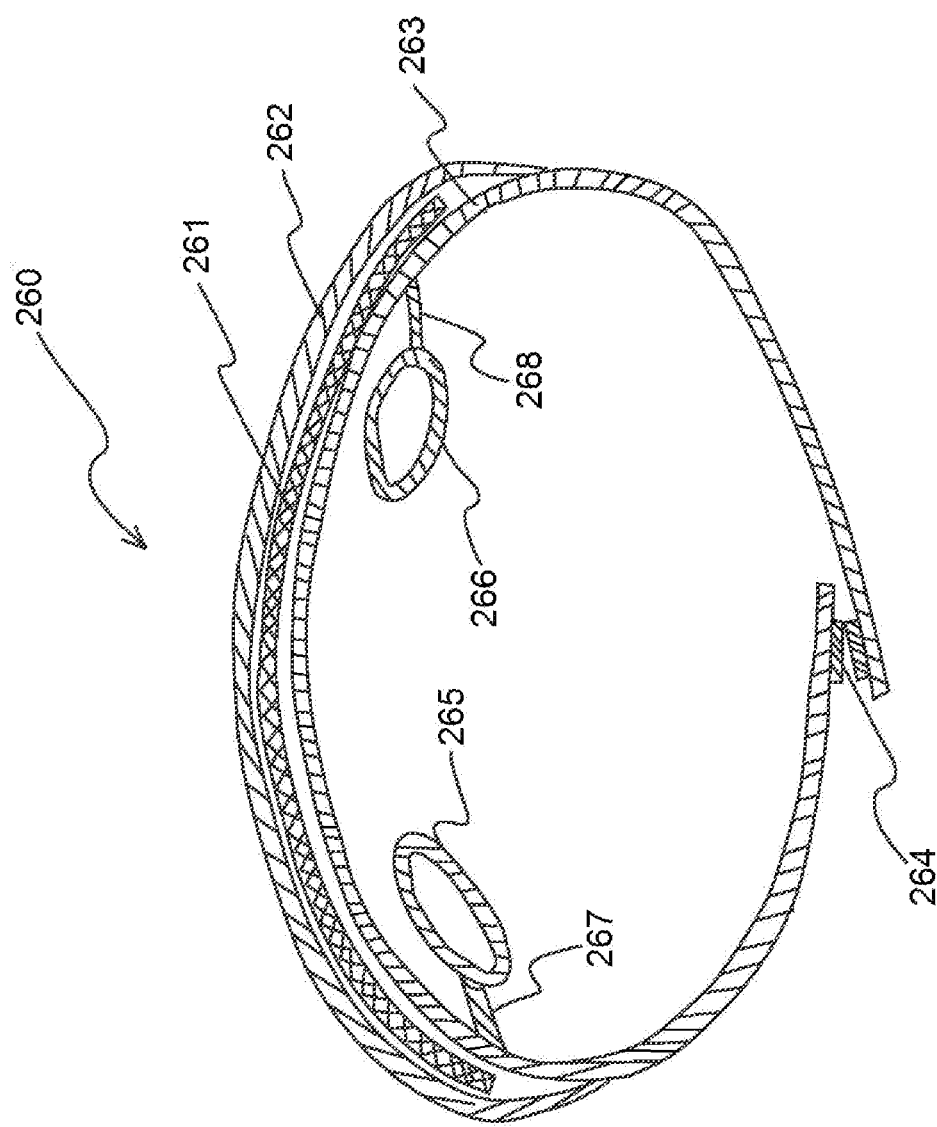
FIG. 17 is a schematic side view of an embodiment of the hemostatic device comprising two balloons 265, 266 and a compression member 261 that is placed in a sleeve formed by a covering 262 attached to a band 263.

In another embodiment of the invention (See FIG. 17), hemostatic device comprises a flexible band 260. The band has a flexible strap 263 having an inner peripheral side and adapted to be wrapped and secured using binders 264 around a limb of a patient at a site on the limb where bleeding is to be stopped, a compression member 261 having an inner peripheral side, which compression member is made of a material more rigid than the band and at least a portion of the compression member is curved toward its inner peripheral side at proximal and distal ends of the compression member. In one embodiment, the compression member 261 is placed in a sleeve formed by a covering 262 attached to the strap 263. In another embodiment, both the covering 262 and the strap 263 are made of flexible plastic and are transparent. The sleeve can be attached to strap using known techniques, for example ultrasonic welding. A first balloon 265 which is provided on the inner peripheral side of the strap near the proximal end of the sleeve and which inflates when a fluid is introduced therein, and a second balloon 266 which is provided on the inner peripheral side of the strap near the distal end of the sleeve and which inflates when a fluid is introduced therein.

In another embodiment, the band and the compression member are substantially transparent. In yet another embodiment, at least the first or the second balloon is connected to the band using connectors 267 and 268.

Figure 18:
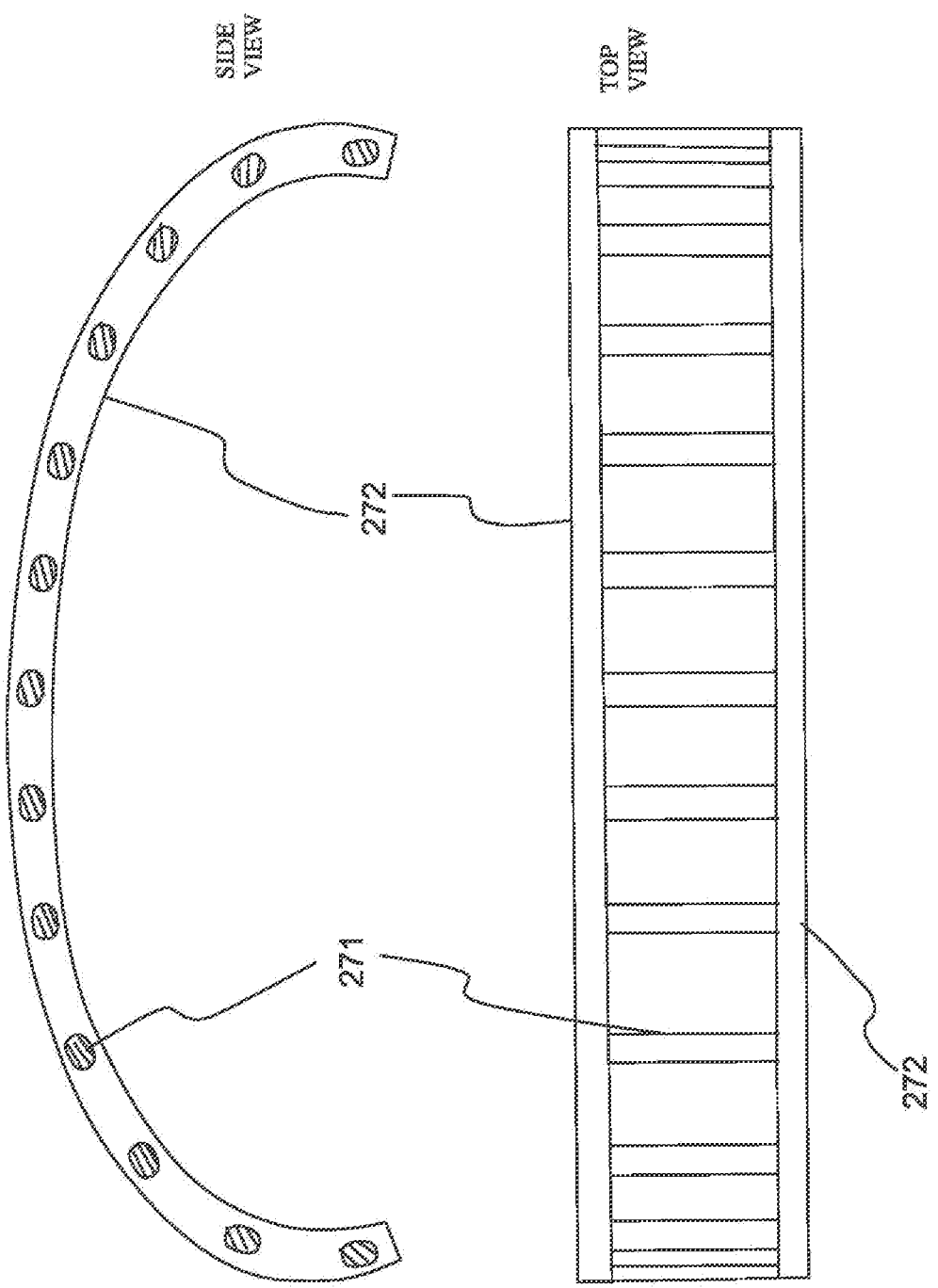
FIG. 18 is a schematic side view and top view of an embodiment of the compression member comprising rungs 271 located between two beams 272.

FIG. 18 is a schematic side view and top view of an embodiment of the compression member comprising rungs 271 located between two beams 272. The compression member has the shape of a curved ladder, and at least a portion of the compression member is curved toward the inner peripheral side at proximal and distal ends of the compression member. The rungs of the ladder may be equidistant from each other along the axis of the ladder or the rungs may be staggered whereby some rungs are close to each other while the others are spread out. Further, the rungs of the ladder may all be located along the curved axis of the ladder, or the rungs may be located on either side of the axis whereby the rungs are positioned as a wave along the curved axis of the ladder. In one embodiment, a crest of the wave formed by the rungs presses on an inflatable balloon that compresses an artery. The cross section of the beam 272 can have different shapes, e.g., circular, rectangular, square, elliptical, or I-section.

Figure 19:
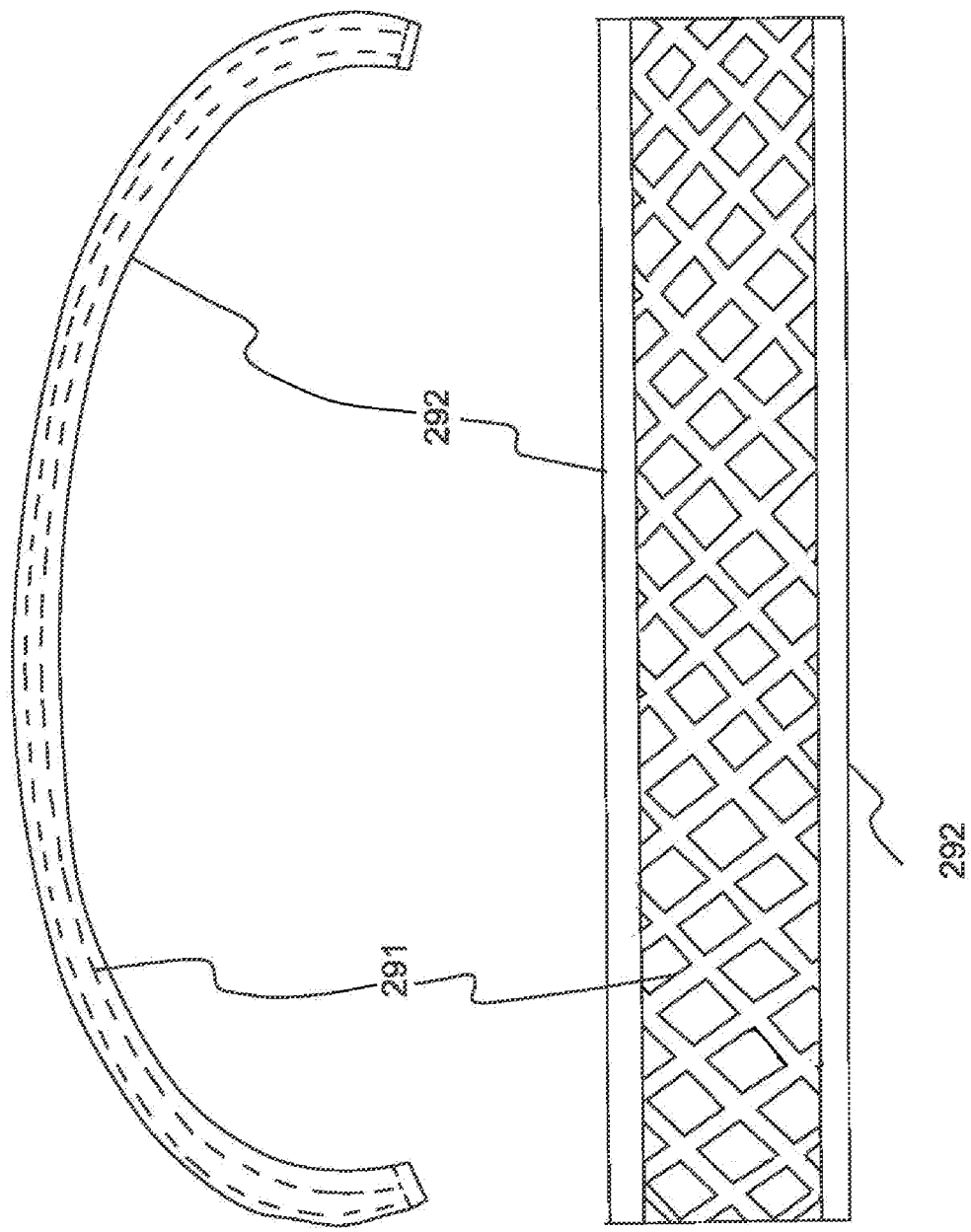
FIG. 19 is a schematic side view and top view of an embodiment of the compression member comprising a lattice 291 located between two beams 292.

FIG. 19 is a schematic side view and top view of an embodiment of the compression member comprising a lattice 291 located between two beams 292. The compression member has the shape of a curved lattice, and at least a portion of the compression member is curved toward the inner peripheral side at proximal and distal ends of the compression member. The lattice may have a curved shape identical to the curved shape of the two beams and located along the curved axis of the two beams 292 as shown in FIG. 19, or the lattice may have a wavy form whereby the crests and valleys of the lattice touch inner peripheral side and outer peripheral side of the two beams 292. In one embodiment, a crest of the wave formed by the lattice presses on an inflatable balloon that compresses an artery. The cross section of the beam 292 can have different shapes, e.g., circular, rectangular, square, elliptical, or I-section.

In one embodiment, a combination of a ladder and a lattice may be used for the compression member. In another embodiment, the compression member may have a contoured shape whereby the band holds snugly around the wrist and the contoured shape facilitates compression of the ulnar artery at the base of the palm.

In another embodiment, the internal pressure of the inflated balloon is decreased over time, thereby reducing the compressive force applied by the balloon, thus enabling the prevention of harm from sustained compressive force, such as numbness, pain or vascular occlusion.

Figure 20:
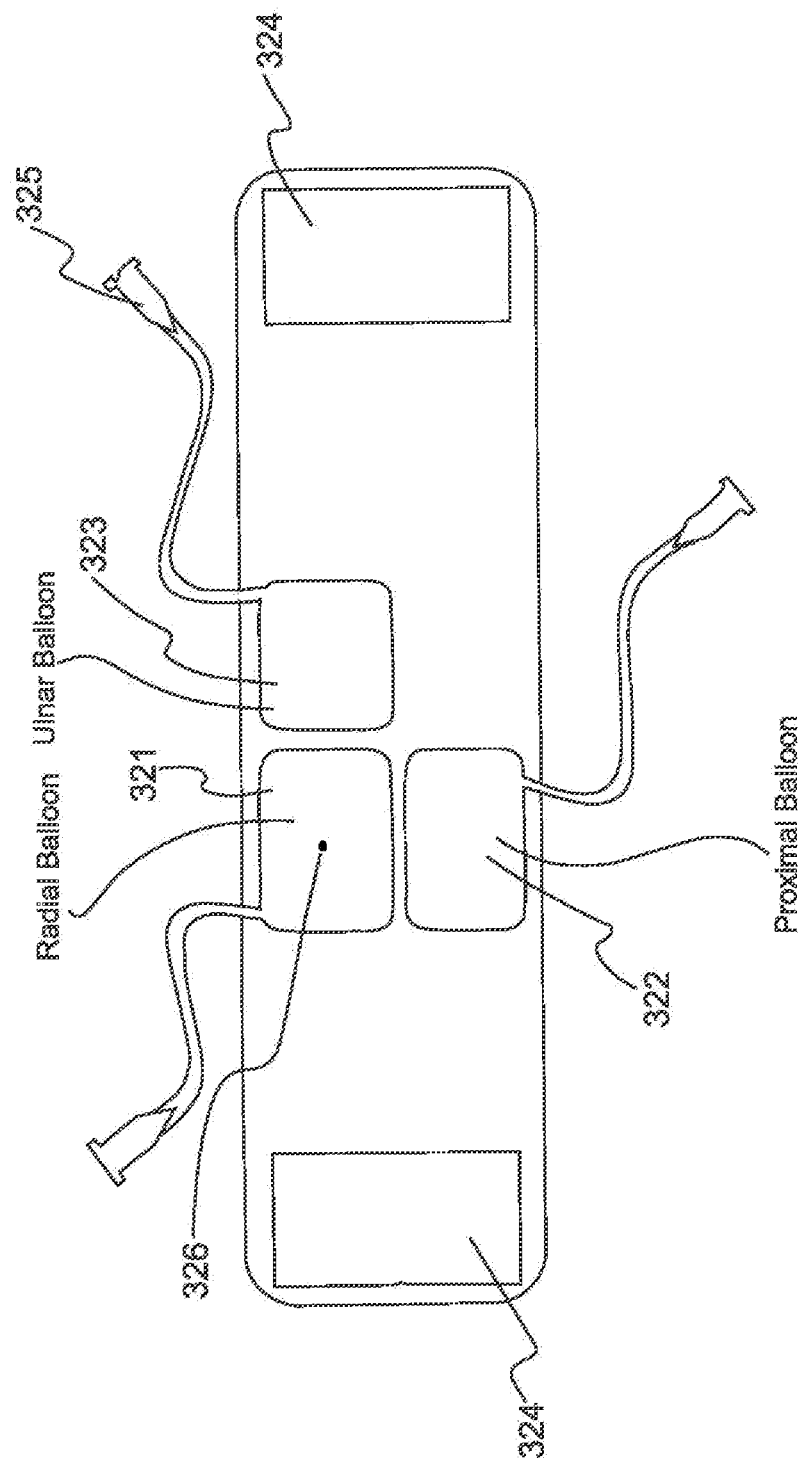
FIG. 20 is a bottom view of an embodiment of the hemostatic device comprising at least three balloons.

In one embodiment, the hemostatic device comprises a band (see FIG. 20) that has at least three inflatable balloons (321, 322, and 323), placed side by side, forming an "L-shaped" configuration. In one embodiment, each balloon is inflatable independent of the other two balloons. Inflation of these balloons can be achieved using a fluid under pressure. In one embodiment, the fluid is air. The band has an anchoring mechanism to hold the band around a limb. The anchoring mechanism may be Velcro strap (324), a latch or any other tie down. In one embodiment, the anchoring mechanism is placed on the portion of the band away from the balloons. A marker (326) is placed on the balloon that is placed at the arterial puncture site ("puncture site balloon") (321) to center the pressure applied by the "puncture site balloon" at the arterial puncture location. In another embodiment, the tubing connected with the cavity of each of the three balloons has a luer-lock end (325), with a 2-way stop-cock valve to allow for connection to a luer-lock syringe, and the stop cock giving the ability to prevent balloon deflation. In yet another embodiment, soft "pledgets" are placed to allow on the two straps of the band for cushioning against the skin and allow for venous drainage. In another embodiment, a 20 ml syringe with luer-lock tip is provided to inflate and deflate the balloons.

The band may be made out of plastic, cloth or any other suitable material. In one embodiment, at least a part of the band that is placed over the puncture site is made of transparent material. In another embodiment, the entire band is made of transparent material.

In one embodiment, a method to obtain hemostasis provides compression of the ipsilateral ulnar artery "before or at the time of" removal of radial artery introducer or catheter. After the ulnar artery is compressed, occluded, lack of antegrade ulnar flow is verified by using any available technique to detect ulnar flow. The radial artery is then compressed at any point proximal to the puncture site thereby decreasing radial artery pressure as well as flow at the radial artery puncture site. The radial artery introducer/catheter is then removed, and required pressure is applied to stop visible bleeding at the puncture site. Antegrade radial artery flow is continuously monitored and pressure at the radial artery site proximal to the puncture site is adjusted to maintain/re-establish antegrade radial artery flow, as well as dry hemostasis at the puncture site using the least necessary pressure at the radial artery puncture site. Once this combination is achieved, the device is left in place for typically 10-15 minutes although the duration is based on operator judgment, after which the puncture site compression pressure is released gradually till there is no pressure applied at the puncture site. After a short duration, usually 5-10 minutes of achieving this, the proximal compression pressure is gradually decreased, till there is no pressure applied proximally. After a short duration (another 5-10 minutes), the ulnar artery compression pressure is released, and the radial artery puncture site is dressed with light dressing.

Figure 21:
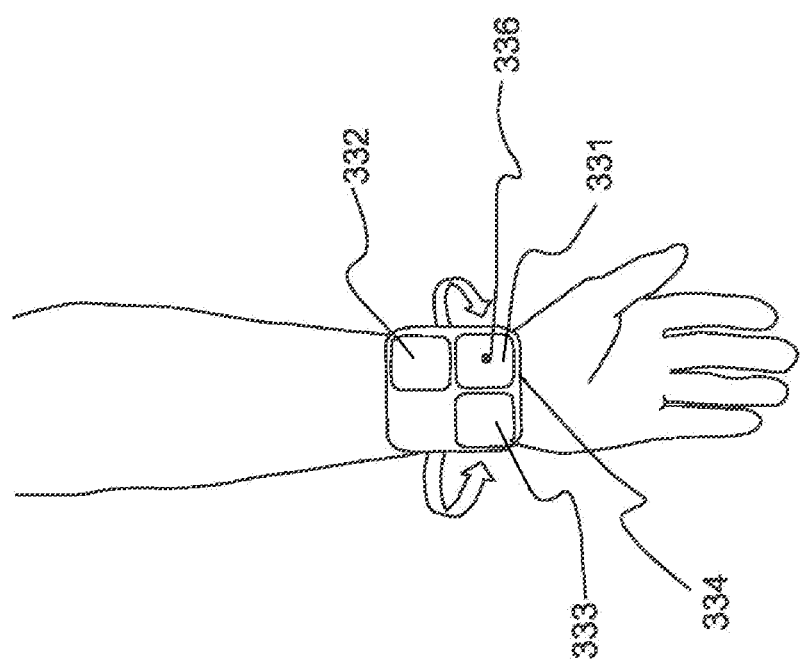
FIG. 21 is a schematic view of an embodiment of the hemostatic device applied on a forearm of a patient. The three balloons (331, 332 and 333) are located between the forearm of the patient and the band that goes around the forearm of the patient.

In another embodiment, a method to obtain hemostasis comprises steps described below (See FIGS. 20 and 21):

Step 1: Apply the triple balloon band (334) on the field of interest of the involved forearm. Place the marker (326, 336) on the "puncture site balloon" at or near the arterial puncture site. Secure the Velcro attachments (324), with the free ends of the band encircling the forearm, so that the band is tightly in contact with the patient's skin.

Step 2: Inflate the balloon (323, 333) located over the ulnar artery with about 15 ml of air and measure ulnar artery antegrade flow. Any method including plethysmography that are customary in the medical practice may be used for measurement of flow.

Step 3: Withdraw the radial artery introducer/catheter, so that <3 cm of the introducer/catheter remains in the arterial lumen. Inflate the balloon (322, 332) that is proximal to the puncture site balloon (321, 331) to a pressure level that provides occlusive compression of the radial artery proximal to the puncture site. Remove the introducer/catheter from the radial artery, deflate the proximal balloon just enough to allow mild bleeding at the puncture site, verifying re-establishment of flow in the radial artery, and promptly inflate the puncture site balloon (321, 331) to stop the mild bleeding. If bleeding persists after applying mild pressure with puncture site balloon (321, 331), inflate the proximal balloon (322, 332) further, to stop bleeding. Leave the ulnar balloon (323, 333) inflated with occlusive ulnar compression throughout this process.

Step 4: Leave the band on for 10-15 minutes. Then deflate the puncture site balloon (321, 331) gradually to zero pressure. Leave the band on for an additional 10-15 minutes.

Step 5: Deflate proximal balloon (322, 332) gradually to zero pressure. Leave the band on for 5 minutes and then deflate the ulnar balloon (323, 333) and remove the band. Apply light dressing at the puncture site.

In one embodiment of the invention, efficacy for hemostasis is provided with short duration of compression at the puncture site, thereby reducing the risk of radial artery occlusion. In another embodiment, pressure and flow are modulated at the puncture site by compressing at locations away from the puncture site. In yet another embodiment, hemostasis is achieved using a pressure at the puncture site that is lower than previously known or used in the art. In yet another embodiment, hemostasis is achieved while maintaining mobility of the patient's hand.

In another embodiment of the invention (See FIG. 22), hemostatic device comprises a flexible band (341) adapted to be wrapped and secured around a hand of a patient at a site on the hand where bleeding is to be stopped, a curved plate (342) having an inner peripheral side, which plate is made of a material more rigid than the band and at least a portion of the plate is curved toward the inner peripheral side at proximal and distal ends of the plate, a first balloon (343) which is provided on the inner peripheral side of the curved plate near its proximal end and which inflates when a fluid is introduced therein, a first pressing member (344) which is provided between the curved plate and the first main balloon so that at least a portion thereof overlaps with the first balloon and which is adapted for pressing against the first balloon, and a second balloon (345) which is provided on the inner peripheral side of the curved plate near its distal end and which inflates when a fluid is introduced therein, a second pressing member (346) which is provided between the curved plate the second main balloon so that at least a portion thereof overlaps with the second balloon and which is adapted for pressing against the second balloon.

In another embodiment, the band and the curved plate are substantially transparent. In yet another embodiment, at least the first or the second balloon is connected to the band using connectors 347 and 348. In another embodiment, at least the first or the second balloon is communicably connected to corresponding pressing member.

Figure 23:
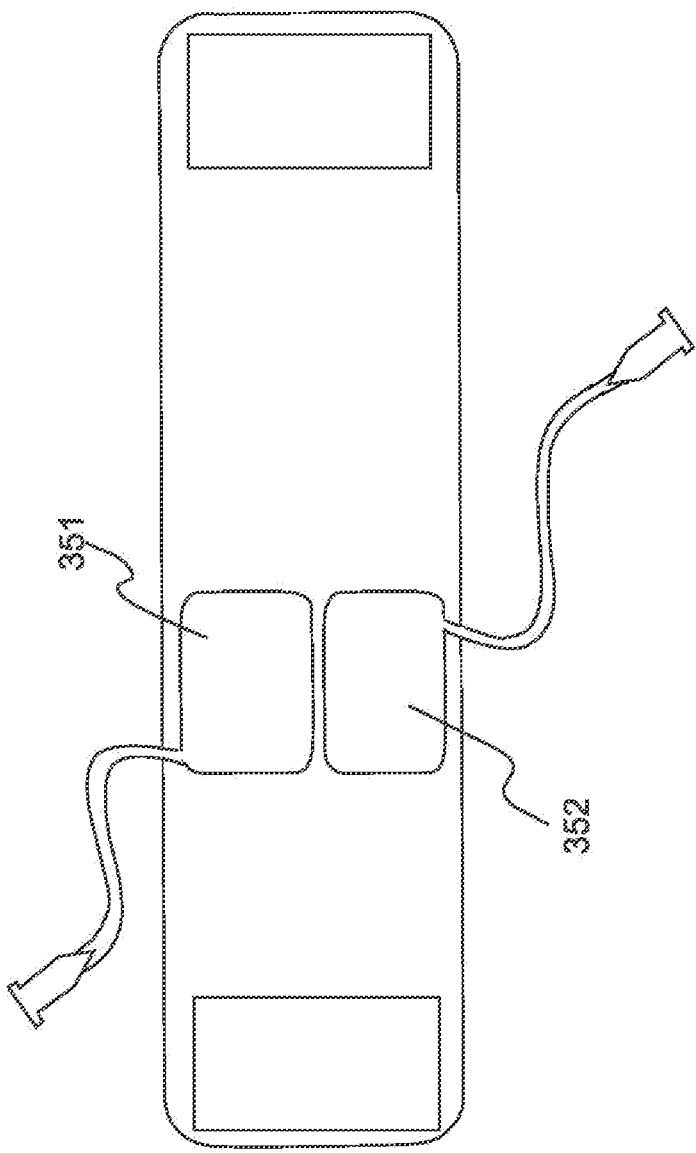
FIG. 23 is a bottom view of an embodiment of the hemostatic device comprising two balloons in a configuration to compress the same artery at two locations.

In one embodiment (See FIG. 23), the band comprises two balloons—one balloon (351) located for placement over the puncture site of an artery, e.g., radial artery and the other balloon (352) located for placement on the same artery upstream of a puncture site. The pressure applied on the puncture site of the artery and pressure applied upstream of the puncture site could be simultaneously manipulated to optimize the pressure at which the bleeding from the artery stops while at the same time a high enough pressure is applied to the artery upstream of the puncture site to prevent or minimize occlusion of the artery and facilitate formation of a geometrically stable thrombus plug.

Figure 24:
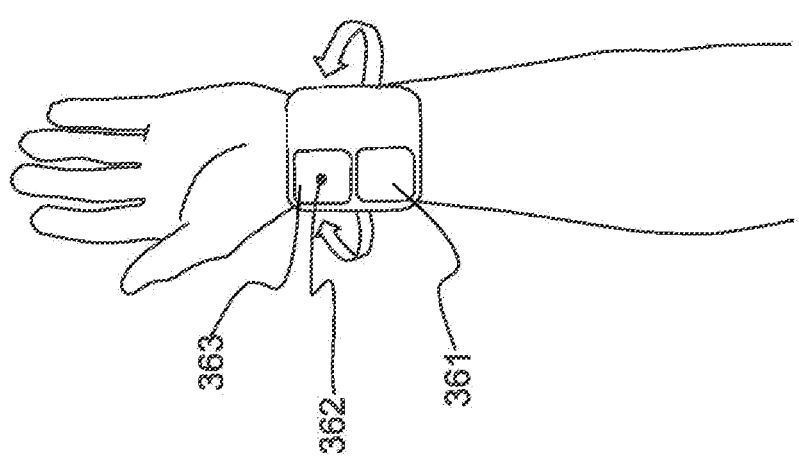
FIG. 24 is a schematic view of an embodiment of the hemostatic device comprising two balloons located proximally and distally and compressing same artery when applied on a forearm of a patient.

In one embodiment (see FIG. 24), a method to obtain hemostasis involves compressing the un-instrumented portion of the artery "proximal" or upstream from the puncture site using balloon 361, in order to reduce the flow and pressure through the artery at the site of the puncture 362. After compressing the proximal segment of the artery, the puncture site is compressed using balloon 363, to achieve hemostasis. Typically, much lower pressure is required to stop extravasation, leading to lesser flattening of the artery, and lesser separation of the arterial wall edges, hence the arteriotomy has a more favorable geometry of a smaller and "deeper" rent, as opposed to a wider and shallower rent with higher pressure. This leads to a shorter duration of compression, at lower pressure, with higher probability of maintaining flow, and formation of a geometrically more stable thrombus plug. The artery is compressed at the puncture site using non-occlusive pressure. The absence of occlusion may be verified by any means available to document presence of flow at the puncture site. Adequacy of hemostasis is monitored closely, and compression is removed when hemostasis is felt to be stable without compression.

In one embodiment, the band may have near the center thereof a curved plate. The curved plate may be placed in a curved plate holder. The curved plate holder is composed in part of a separate strip-like member joined to the outside (or inside) surface of the band by a suitable method such as welding (e.g., heat welding, high-frequency welding, ultrasonic welding) or adhesion (such as with adhesive or solvent) so as to form a double layer construction. The curved plate is inserted into a gap in the double layer and thereby held. The curved plate is shaped so that at least a portion thereof is curved toward an inner peripheral side of the plate.

Figure 25:
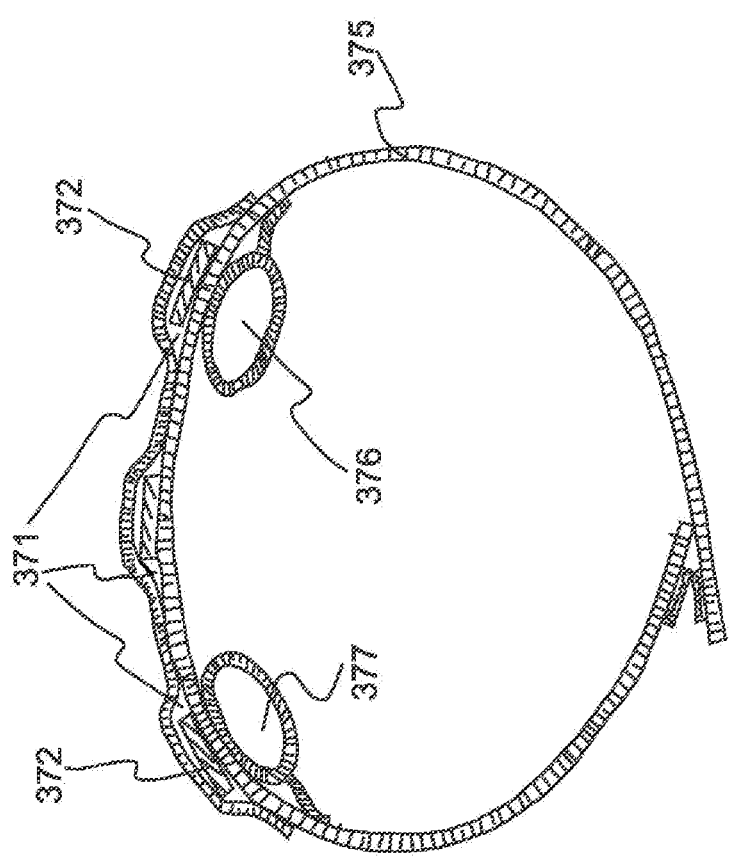
FIG. 25 is a schematic view of an embodiment of the hemostatic device comprising at least two gaps provided on the band using a double layer construction and flat plates inserted in the gaps, with balloons located under the flat plates.

In another embodiment (see FIG. 25), at least two gaps (371) are provided on the band (375) using a double layer construction as described above and flat plates (372) are inserted in the gaps. In one embodiment, balloons (376 and 377) are located under the flat plates. In yet another embodiment at least one gap is provided over the location of a balloon to insert a flat plate over the balloon. In one embodiment, the plate (curved or flat) is constructed of a material more rigid than the band and maintains a substantially fixed shape. The material making up the plate is not subject to any particular limitation. In some embodiment, the material is transparent. Examples of materials of which plates may be made include acrylic resins, polyvinyl chloride (particularly rigid polyvinyl chloride), polyolefins such as polyethylene, polypropylene and polybutadiene, polystyrene, poly(4-methyl-1-pentene), polycarbonates, ARS resins, polymethyl methacrylate (PMMA), polyacetals, polyarylates, polyacrylonitriles, polyvinylidene fluorides, polyionomers, acrylonitrile-butadiene-styrene copolymers, polyesters such as polyethylene terephthalate (PET) and polybutylene terephthalate (PBT), butadiene-styrene copolymers, aromatic and aliphatic polyamides, and fluoro-carbon resins such as polytetrafluoroethylene.

The method of providing plates on the band is not limited to the illustrated arrangement and may involve joining the plate(s) to the inside surface or outside surface of the band by a suitable method such as welding or adhesion. It is not necessary that the band encircle the limb, e.g., wrist completely. For example, another arrangement may be the band is held in place by tie down that holds the band firmly on the wrist.

Figure 26:
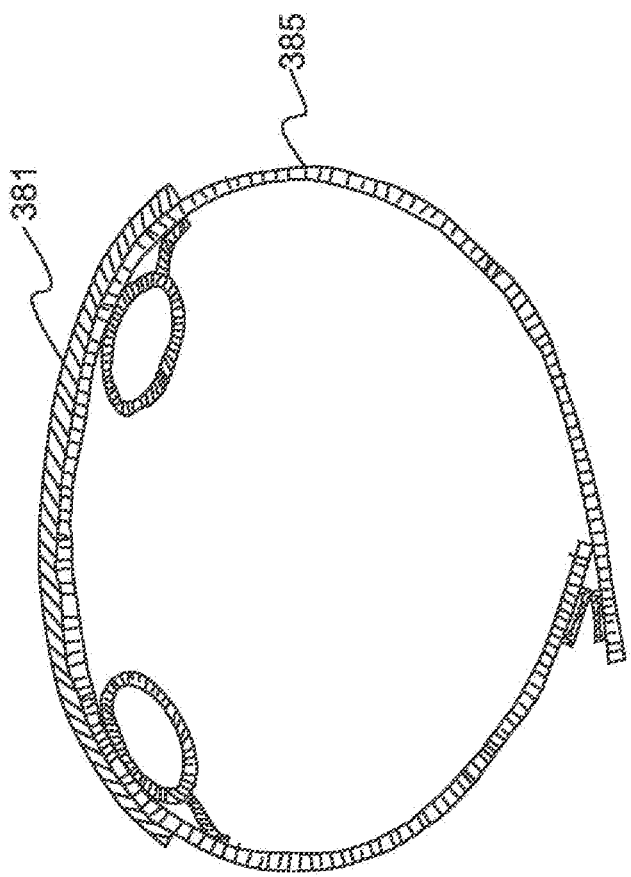
FIG. 26 is a schematic view of an embodiment of the hemostatic device comprising a layer of material that is more rigid than the band material affixed to outside of the band in the central portion of the band.

In yet another embodiment (see FIG. 26), a layer (381) of material that is more rigid than the band material is affixed to outside of the band in the central portion of the band (385). The layer of rigid material may also be affixed to inside of the band or to both inside and outside of the band. The layer can be affixed using commonly used techniques for lamination, e.g., an adhesive or heat treatment. The balloons are located under the rigid portion of the band and the rigidity facilitates compression of the balloon against the patient's limb. In another embodiment, the band does not have any rigid plate inserts or any layers attached to enhance rigidity.

The balloon may have a construction in which the edges of sheets are sealed together by a suitable process such as welding or adhesion to form a pouch. In one embodiment, the balloons are square in shape. The balloon may be connected to the band using a flexible connector. In one embodiment the connector may be made of the same material as the balloon. In another embodiment the connector may be short thereby keeping the balloon tethered to the band at a position. In another embodiment, the connector may be long thereby giving the user flexibility in the placement of the balloon.

Figure 22:
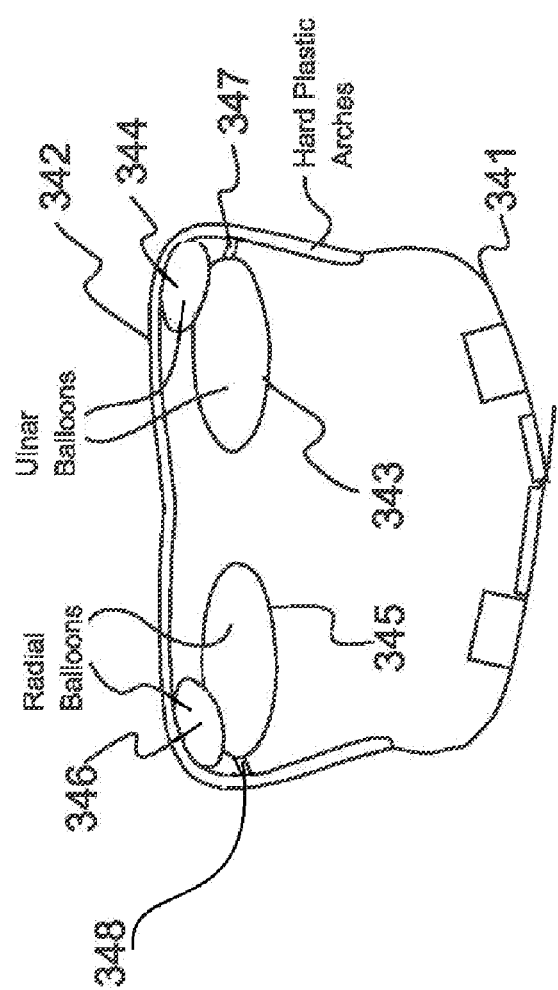
FIG. 22 is a schematic side view of an embodiment of the hemostatic device comprising two balloons and two pressing members.

As shown in FIG. 22, a pressing member (a secondary balloon) may be provided with a primary balloon that touches the skin of the patient. The secondary balloon is located between the band and the primary balloon in such a way that all or part of the secondary balloon overlaps with the main balloon. The secondary balloon functions as a pressing member for pressing against the main balloon. The material and construction of the secondary balloon may be same as that of the main balloon. In one embodiment, the secondary balloon is smaller in size than the main balloon. In another embodiment, the secondary member is fluidly connected to the primary member whereby introduction of a fluid in the primary member inflates the primary member as also the secondary member.

Figure 27:
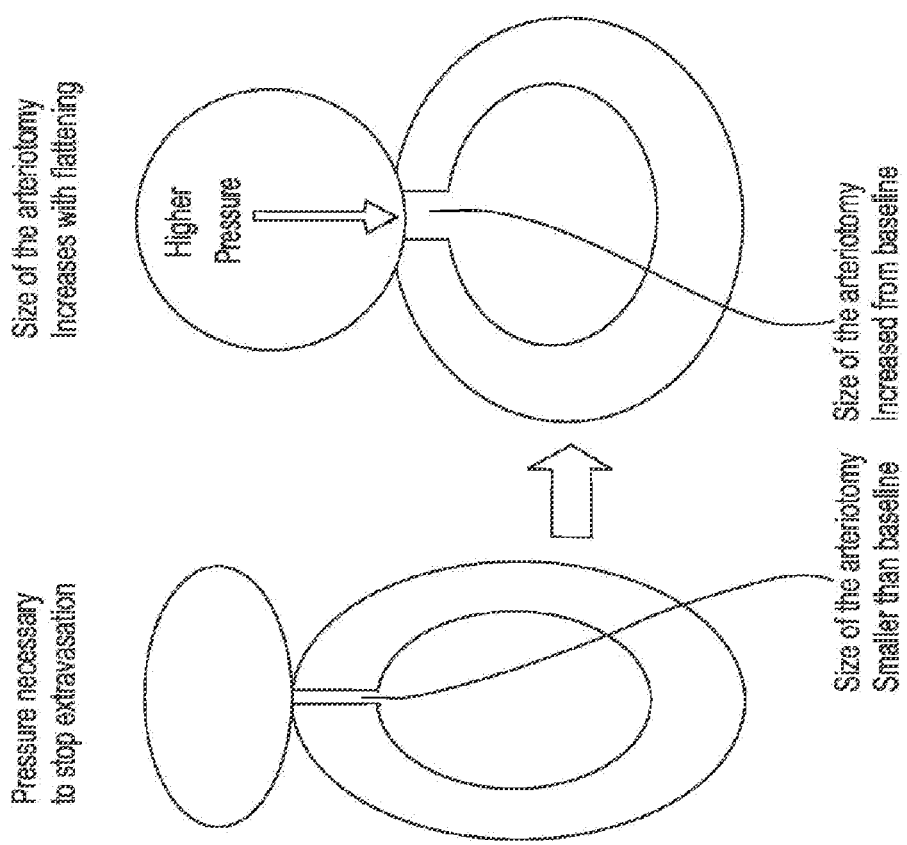
FIG. 27 is a schematic view showing the effect of higher pressure on arteriotomy.
Figure 28:
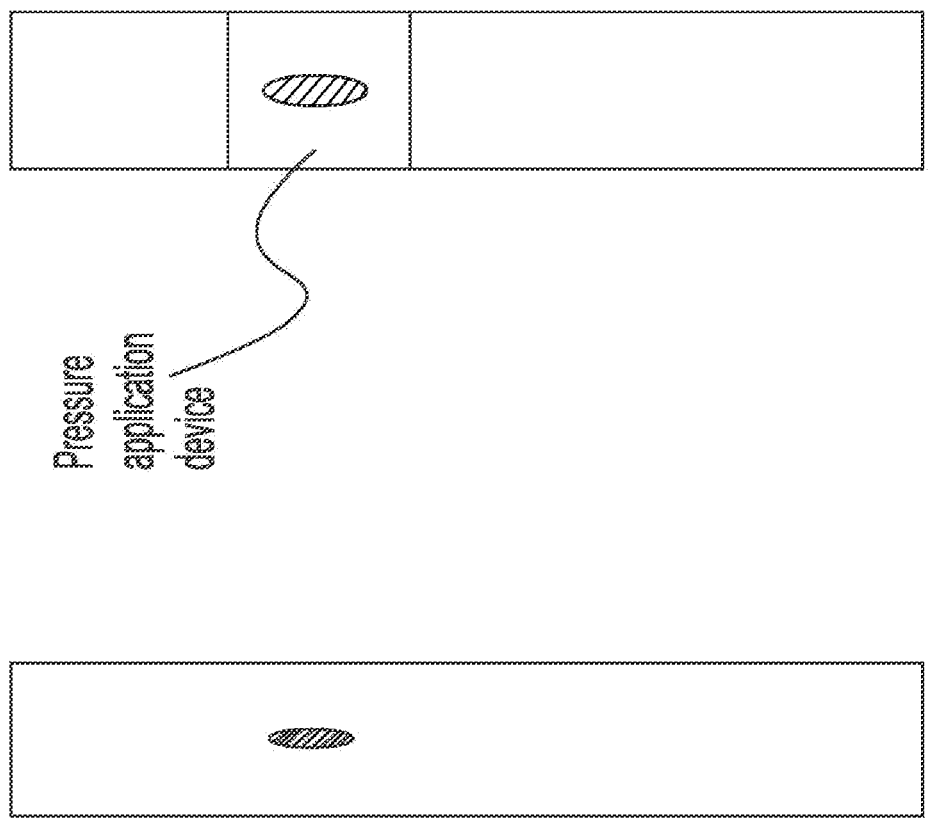
FIG. 28 is a schematic view showing flattening and enlargement of arteriotomy by pressure.
Figure 29:
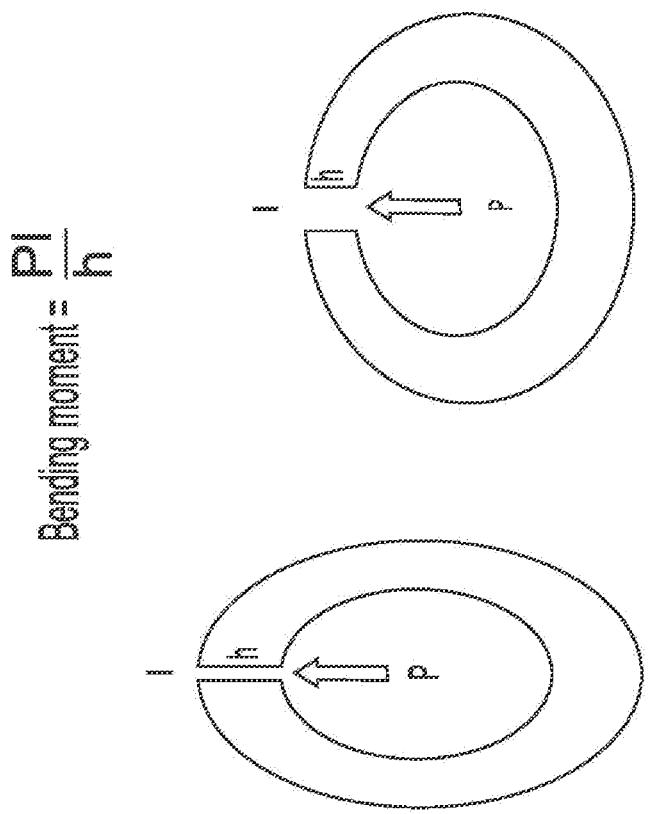
FIG. 29 is a schematic view showing the principle of bending moment.

Application of direct pressure at the puncture site, most effective if perpendicular to the plane of the puncture, has multiple effects on the arterial wall. Pressure leads to compression of the artery in the plane parallel to the direction of the force, leading to "ellipsoidal" deformation of the artery with expansion of the contour in the plane perpendicular to the direction of the force (See FIG. 27). This may lead to stretching and expansion of the arteriotomy from its native state (See FIG. 28), both by direct compression related expansion at the site of puncture and compounded by increase in azimuthal stress in an ellipse compared to a circular contour. The expansion of the arteriotomy by flattening effect of application of pressure is related to the magnitude of force applied, with larger separation of the edges more likely with higher pressure. Separation of the edges, increases the horizontal dimension of the thrombus plug needed to seal the residual arteriotomy, increasing the duration required to form this thrombus, and also decreases the ability of the thrombus to resists dislodgement as a result of the outward push from arterial intraluminal pressure. By the principles of "bending moment" the ratio of anchoring surface to the span of a rectangular structure bridging a gap has an exponential relationship to its weight bearing ability or bending moment. Hence thrombus plugs that are "long and narrow" have more strength, compared to those that are "wide and thin" (See FIG. 29).

Figure 30:
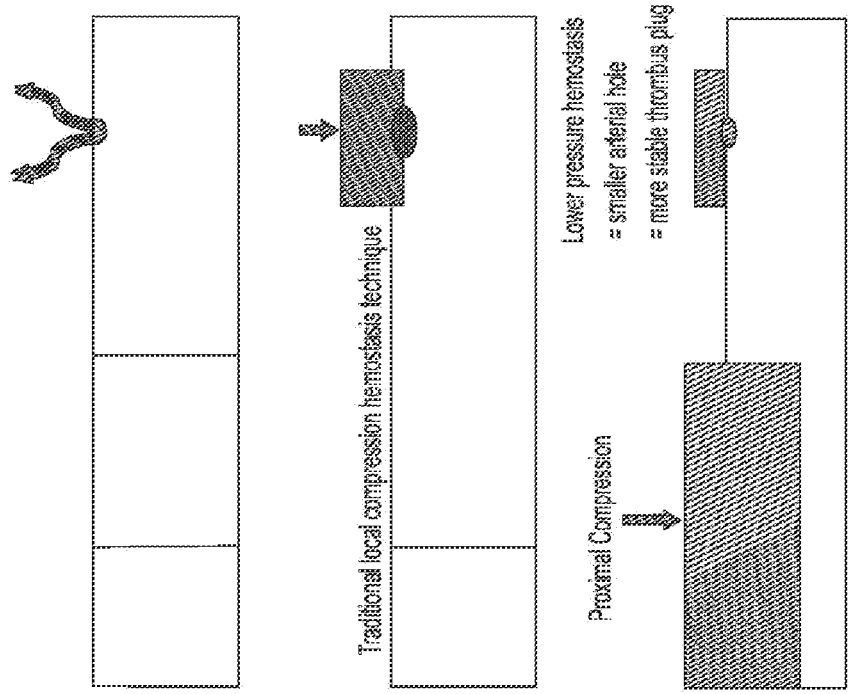
FIG. 30 is a schematic view showing proximal compression and lower pressure hemostasis.

An embodiment of the invention is a method that involves compressing the un-instrumented portion of the artery "proximal" or upstream from the puncture site, in order to reduce the flow and pressure through the artery at the site of the puncture. After compressing the proximal segment of the artery, the puncture site is compressed with the traditional means, to achieve hemostasis. Typically, lower pressure is required to stop extravasation, leading to lesser flattening of the artery, and lesser separation of the arterial wall edges, hence the arteriotomy has a more favorable geometry of a smaller and "deeper" rent, as opposed to a wider and shallower rent with higher pressure. This leads to a shorter duration of compression, at lower pressure, with higher probability of maintaining flow, and formation of a geometrically more stable thrombus plug. The act of compressing an un-instrumented artery leads to mechanical effects without activation of endothelial dependent post-traumatic cascades. The procedure is as follows (See FIG. 30):

STEP 1: After any arterial instrumentation involving arterial puncture, compression using any modality or instrument is applied to any or entire segment of the artery proximal or upstream from the site of puncture. The artery is compressed using non-occlusive pressure. The absence of occlusion may be verified by any means available to document presence of flow at the puncture site.

STEP 2: Local compression at the puncture site is then applied using any available modality, with least necessary pressure applied to stop extravasation of blood.

STEP 3: The compression pressure at the "proximal" segment is maximized to reduce the pressure required at the puncture site to the lowest possible pressure allowing coexistence of forward flow at the puncture site, and dry hemostasis.

STEP 4: Adequacy of hemostasis is monitored closely, and continuous presence of antegrade flow at the puncture site and distal to the puncture site is assessed and established, by any of the available means (e.g., Plethysmography, ultrasound, Doppler).

STEP 5: Compression is removed when hemostasis is felt to be stable without compression.

An embodiment of the band of the present invention is used in a method directed at minimizing occurrences of radial artery occlusion during the catheterization procedure of the radial artery. Once the catheterization procedure is complete, an ulnar pressure is applied to the ipsilateral ulnar artery at an ulnar pressure site while a sheath, e.g., a catheter, remains inserted in the radial artery. The sheath is then removed from the radial artery while maintaining the pressure to the ulnar artery. Once the sheath is removed, and while continuing to apply the ulnar pressure, pressure is applied to the radial artery at the access site to obtain hemostasis at the access site.

The radial artery and the ulnar artery are the two conduits for the flow of oxygenated blood to the hand. The arteries are interconnected and therefore form an interdependent flow network. When flow is reduced in one of the arteries, by compression for example, flow increases in the other artery. When the ulnar artery is compressed, flow in the ulnar artery is reduced, which causes an increase in pressure and flow in the radial artery.

In an embodiment, a further step includes confirming that the application of ulnar pressure has reduced blood flow through the ulnar artery. This is done by monitoring flow of the ulnar artery prior to and after applying the ulnar pressure. In a further embodiment, monitoring flow of the ulnar artery includes sensing skin blood flow and/or pulsation at a fingertip or other location downstream of the ulnar pressure site. Digital plethysmography is employed in one embodiment.

In another embodiment, the method further includes confirming patency of the radial artery during the step of applying a pressure to the radial artery. Confirmation of patency is accomplished by sensing skin blood flow and/or pulsation at a fingertip or other location downstream of the access site. Other sensing locations both upstream and downstream may be used to confirm patency of the radial artery. In one embodiment, the sensing is performed while the ulnar artery is fully compressed (allowing no flow through the ulnar artery) and/or partially compressed (allowing less flow than when not compressed at all). Patency is confirmed, in an embodiment, by obtaining a metric relating to the sensing and comparing the metric with a standard metric for the patient, or with a previously-sensed metric. Metric is understood to mean a sensible, quantifiable value or reading, relating to the characteristic sensed. Preferably, the previously sensed metric is read after applying the ulnar pressure step and before the step of removing the sheath from the radial artery. Digital plethysmography may be employed to obtain the metrics. Other sensing modes may be employed, so long as the selected mode is capable of confirming patency in one form or another.

EXAMPLE 1

A band was fabricated from a substantially transparent polyvinyl chloride sheet material having a thickness of 0.5 mm. The band had a length of 240 mm and a width of 55 mm. A radial artery balloon and an ulnar artery balloon were each fabricated from a substantially transparent polyvinyl chloride sheet material having a thickness of 0.25 mm. The radial artery balloon had the dimension of 38 mm×55 mm and the ulnar artery balloon had the dimension of 38 mm×38 mm. The radial artery balloon, ulnar artery balloon and band were welded together at the necessary places to form a hemostatic device having the construction according to FIG. 5. Two adapters with check valves were connected to the two balloons via ducts as shown in FIG. 5. The adapters were configured to lock with a luer lock syringe. A curved frame was made of 2 mm diameter rungs, with spacing between the rungs of 2 mm (center to center distance between the rungs was 4 mm). The rungs were held between two parallel beams of diameter 3 mm. The frame was curved at both ends and had identical radius of curvature at both ends. The radius of curvature at each end was 20 mm. The frame had a center portion that was straight and had a length of 28 mm. The width of the frame was 52 mm. The frame was constructed according to FIG. 2. Hook and loop (Velcro) fasteners were used to fasten. This hemostatic device was wrapped around the wrist of normal volunteers and the two balloons were inflated by injecting air into the balloons using a 20 mL syringe with a luer lock. It was observed that inflation of the radial balloon did not influence perfusion of the fingers via the ulnar artery. A 20 mL inflation of the radial artery balloon lead to complete obliteration of antegrade radial flow, although there was no influence on perfusion through the ulnar artery. On the ulnar side, with a shorter width (38 mm) balloon, full 15 mL inflation of ulnar balloon did not influence the status of flow in the radial artery.

Any constricting girdle-like device would be expected, even at a lower pressure to first constrict the veins and cause venous congestion in the fingers. It was surprising to observe a complete lack of venous congestion, and no symptoms of venous congestion were reported by any of the volunteers. On several occasions, 2 hour application of the band was performed as would be performed clinically for hemostasis. Venous congestion did not occur. Symptoms related to pressure at the ulnar tuberosity were also not reported by the volunteers. This is likely because of (i) focal pressure application by the orientation of the balloons, leaving probably enough soft tissue space (in the central compartment of the forearm where most large veins are located) for the venous return to occur, and (ii) a decrease in magnitude of required pressure because of the design features such as orientation and sizes of the two balloons, their location in the band, and the shape and structure of the frame.

COMPARATIVE EXAMPLE 2

A band similar to that used in EXAMPLE 1 was fabricated, the only difference being, in COMPARATIVE EXAMPLE 2, the width of the ulnar balloon was nearly the same as the width of the band. In EXAMPLE 1, the ulnar balloon had a width of 38 mm, which is about 70% of the width of the band. With the larger ulnar balloon of COMPARATIVE EXAMPLE 2, inflation of the ulnar balloon was noted to influence the perfusion of radial artery. This was particularly pronounced in small forearms where the larger ulnar balloon may assume an orientation such that the force applied to the wrist when the ulnar balloon is inflated impacts the radial artery.

Tests have shown that the location of the ulnar balloon on the forearm aspect of the band increased the efficacy of the balloon to compress and occlude ulnar artery. Moving the balloon towards the hand and especially gluing it to the palmar aspect of the band increased the efficacy of the ulnar balloon to focally compress and occlude ulnar artery without any other effects or symptoms.

It will be appreciated that several of the above-disclosed and other features and functions, or alternatives or varieties thereof, may be desirably combined into many other different systems or applications. Also that various alternatives, modifications, variations or improvements therein may be subsequently made by those skilled in the art which are also intended to be encompassed by the following claims.

In the description above, for the purposes of explanation, numerous specific requirements and several specific details have been set forth in order to provide a thorough understanding of the embodiments. It will be apparent however, to one skilled in the art, that one or more other embodiments may be practiced without some of these specific details. The particular embodiments described are not provided to limit the invention, but to illustrate it. The scope of the invention is not to be determined by the specific examples provided above. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. In another situation, an inventive aspect may include a combination of embodiments described herein or in a combination of less than all aspects described in a combination of embodiments.

The invention claimed is:

1. A hemostatic device comprising:
a flexible band configured to be wrapped around an arm in which a radial artery and an ulnar artery are located, the flexible band possessing a longitudinal extent that extends in a longitudinal direction; a securing portion that secures the flexible band on the arm while the flexible band is wrapped around the arm in a wrapped state;
an inflatable member connected to the flexible band and expandable upon being inflated in response to introducing fluid into an interior of the inflatable member to press a part of the radial artery to be subjected to hemostasis, the inflatable member possessing oppositely facing surfaces;
a pressing member disposed at a position spaced from a position of the inflatable member in the longitudinal direction of the flexible band to press the ulnar artery, the pressing member possessing oppositely facing surfaces; and
the pressing member possessing a length along the longitudinal direction of the flexible band that is different than a width of the pressing member along a direction orthogonal to the longitudinal direction of the flexible band.

2. The hemostatic device according to claim 1, wherein the band possesses a width in the direction orthogonal to the longitudinal direction of the band, the width of the pressing member being less than the width of the band.

3. The hemostatic device according to claim 1, wherein the inflatable member possesses a width along a direction orthogonal to the longitudinal direction of the band, the width of the pressing member being shorter than the width of the inflatable member.

4. The hemostatic device according to claim 1, wherein the pressing member is inflatable to outwardly expand when a fluid is injected into the pressing member, and a volume of the inflatable member in an inflated state is larger than a volume of the pressing member in an inflated state.

5. The hemostatic device according to claim 1, further comprising a first tube in communication with the interior of the inflatable member to introduce the fluid into the interior of the inflatable member, and a second tube in communication with an interior of the pressing member to introduce fluid into the interior of the pressing member.

6. The hemostatic device according to claim 1, further comprising a compression member that is more rigid than the flexible band, the compression member being mounted on the flexible band so that the compression member and the flexible band move together as a unit, the compression member including an inner surface that faces toward the arm when the flexible band is wrapped around the arm in the wrapped state, the inner surface of the compression member including a center inner surface portion, a first curved inner surface portion and a second curved inner surface portion, the center inner surface portion being positioned between the first and second inner surface portions along the longitudinal direction of the flexible band, the inflatable member overlapping with the first curved inner surface portion and the pressing member overlapping with the second curved inner surface portion, the center inner surface portion being exposed between the pressing member and the inflatable member.

7. The hemostatic device according to claim 6, wherein the compression member is a frame or a plate.

8. The hemostatic device according to claim 1, further comprising a compression member that is more rigid than the flexible band, the compression member being mounted on the flexible band so that the compression member and the flexible band move together as a unit, the compression member including an inner surface that faces toward the arm when the flexible band is wrapped around the arm in the wrapped state, the inner surface of the compression member including a center inner surface portion, a first curved inner surface portion and a second curved inner surface portion, the center inner surface portion being positioned between the first and second inner surface portions along the longitudinal direction of the flexible band, the inflatable member being connected to the flexible band at a connection, the connection being located so that during use of the hemostatic device, the inflatable member is positioned between the central portion and the first curved inner surface portion.

9. The hemostatic device according to claim 8, wherein the compression member is a frame or a plate.

10. A hemostatic device comprising:
  a flexible band configured to be wrapped around an arm in which a radial artery and an ulnar artery are located, the flexible band possessing a longitudinal extent that extends in a longitudinal direction, the flexible band being made of a material; a securing portion that secures the flexible band on the arm while the flexible band is wrapped around the arm in a wrapped state;
  a compression member held by the flexible band and made of a material more rigid than the material from which the flexible band is made;
  an inflatable member connected to the flexible band and expandable upon being inflated in response to introducing fluid into an interior of the inflatable member to press a part of the radial artery to be subjected to hemostasis;
  a pressing member disposed at a position spaced in the longitudinal direction of the flexible band and configured to press the ulnar artery;
  the inflatable member possessing a first surface disposed on a side that will face the arm when the flexible band is in the wrapper state and a second surface disposed on a side facing the band;
  the pressing member including a third surface disposed on a side that will face the arm when the flexible band is in the wrapper state and a fourth surface disposed on a side facing the band; and
  a distance measured as a length of a perpendicular line from the compression member to the first surface is longer than the distance measured a length of a perpendicular line from the compression member to the third surface when the inflatable member and the pressure member are inflated in a state in which at least a part of the second surface of the inflatable portion and at least a part of the fourth surface of the pressing member are in contact with a portion of the band in which the compression member is disposed.

11. The hemostatic device according to claim 10, wherein a surface area of the first surface of the inflatable portion in an inflated state is larger than a surface area of the third surface of the pressing member.

12. The hemostatic device according to claim 10, wherein a length of the pressing member along the longitudinal direction of the band is different than a length of the inflatable portion along the longitudinal direction of the band.

13. The hemostatic device according to claim 10, wherein the pressing member is inflated by being injected with a fluid, and a volume of the inflatable member in the inflated state is larger than a volume of the pressing member in an inflated state.

14. The hemostatic device according to claim 10, wherein the compression member includes an inner surface that faces toward the arm when the flexible band is wrapped around the arm in the wrapped state, the inner surface of the compression member including a center inner surface portion, a first curved inner surface portion and a second curved inner surface portion, the center inner surface portion being positioned between the first and second inner surface portions along the longitudinal direction of the flexible band, the inflatable member overlapping with the first curved inner surface portion and the pressing member overlapping with the second curved inner surface portion, the center inner surface portion being exposed between the pressing member and the inflatable member.

15. The hemostatic device according to claim 10, wherein the compression member includes an inner surface that faces toward the arm when the flexible band is wrapped around the arm in the wrapped state, the inner surface of the compression member including a center inner surface portion, a first curved inner surface portion and a second curved inner surface portion, the center inner surface portion being positioned between the first and second inner surface portions along the longitudinal direction of the flexible band, the inflatable member being connected to the flexible band at a connection, the connection being located so that during use of the hemostatic device, the inflatable member is positioned between the central portion and the first curved inner surface portion.

16. The hemostatic device according to claim 10, wherein the compression member is a frame or a plate.

17. A hemostatic device comprising:
  a flexible band configured to be wrapped around an arm in which a radial artery and an ulnar artery are located, the flexible band possessing a longitudinal extent that extends in a longitudinal direction;
  a securing portion that secures the flexible band on the arm while the flexible band is in a state of being wrapped around the arm;
  an inflatable member connected to the band and expandable upon being inflated in response to introducing fluid into an interior of the inflatable portion to press a part of the radial artery to be subjected to hemostasis, the inflatable member possessing oppositely facing surfaces;
  a pressing member disposed at a position spaced from a position of the inflatable portion in the longitudinal direction of the band to press the ulnar artery, the pressing member possessing oppositely facing surfaces; and
  the pressing member including a main body and a projection disposed on the main body and protruding with respect to the main body.

18. The hemostatic device according to claim 17, wherein the main body is inflatable by being injected with a fluid, the projection communicating with the main body so that the projection inflates together with the main body in response to injection of the fluid, and the projection includes a part protruding outwardly with respect to the main body when the main body and the projection are inflated.

19. The hemostatic device according to claim 17, wherein a length of the projection along the longitudinal direction of the band is shorter than a length of the main body along the longitudinal direction of the band.

20. The hemostatic device according to claim 17, wherein the projection has a shape continuously extending along a direction orthogonal to the longitudinal direction of the band.

* * * * *